(12) United States Patent
Van Emelen et al.

(10) Patent No.: US 7,423,048 B2
(45) Date of Patent: *Sep. 9, 2008

(54) COMPOUNDS FOR TREATING FUNDIC DISACCOMODATION

(75) Inventors: Kristol Van Emelen, Sint-Niklaas (BE); Marcel Frans Leopold De Bruyn, Wortel (BE); Manuel Jesús Alcázar-Vaca, Burguillos (ES); José Ignacio Andrés-Gil, Madrid (ES); Francisco Javier Fernández-Gadea, Bargas (ES); Maria Encamacion Matesanz-Ballesteros, Toledo (ES); José Manuel Bartolomé-Nebreda, Bargas (ES)

(73) Assignee: Janssen Pharmaceutica, N.V., Beerse (BE)

( * ) Notice: Subject to any disclaimer, the term of this patent is extended or adjusted under 35 U.S.C. 154(b) by 0 days.
This patent is subject to a terminal disclaimer.

(21) Appl. No.: 11/355,402

(22) Filed: Feb. 16, 2006

(65) Prior Publication Data
US 2006/0142318 A1    Jun. 29, 2006

Related U.S. Application Data

(62) Division of application No. 10/311,612, filed as application No. PCT/EP01/06749 on Jun. 13, 2001, now Pat. No. 7,081,453.

(30) Foreign Application Priority Data
Jun. 22, 2000   (EP) ................................. 00202180

(51) Int. Cl.
*C07D 413/06* (2006.01)
*C07D 413/14* (2006.01)
*C07D 417/06* (2006.01)
*C07D 417/14* (2006.01)
*C07D 403/06* (2006.01)
*C07D 403/14* (2006.01)
*A61K 31/436* (2006.01)
*A61P 1/14* (2006.01)

(52) U.S. Cl. .................. 514/302; 514/256; 514/252.12; 514/218; 514/212.01; 546/115; 540/484; 540/575; 544/316; 544/359

(58) Field of Classification Search ................ 546/115; 540/484, 575; 544/316, 359; 514/302, 256, 514/252.12, 218, 212.01
See application file for complete search history.

(56) References Cited

U.S. PATENT DOCUMENTS 3,910,930 A    10/1975  Janssen et al. ............... 546/199
7,081,453 B2*   7/2006  Van Emelen et al. ...  514/210.02

FOREIGN PATENT DOCUMENTS

EP           0 004 358 B1     1/1982

(Continued)

OTHER PUBLICATIONS

Arakawa, T. et al., "New Aspects of Gastric Adaptive Relaxation Reflex after Food Intake for More Food: Involvement of Capsaicin-sensitive Sensory Nerves and Nitric Oxide," J. Smooth Muscle Research, 1997, 33(3), 81-88.

*Primary Examiner*—Venkataraman Balasubram
(74) *Attorney, Agent, or Firm*—Woodcock Washburn LLP

(57) ABSTRACT

The present invention concerns compounds of formula (I)

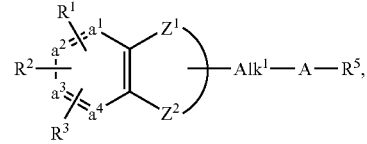

(I)

a stereochemically isomeric form thereof, an N-oxide form thereof or a pharmaceutically acceptable acid addition salt thereof, wherein $-a^1=a^2-a^3=a^4-$ is a bivalent radical wherein one or two of $a^1$ to $a^4$ are nitrogen and the remaining $a^1$ to $a^4$ are $-CH=$; $-Z^1-Z^2-$ is a bivalent radical; -A- is a bivalent radical of formula $-N(R^6)-Alk^2-$ or a 5, 6 or 7-membered saturated heterocycle containing one or two nitrogen atoms; $R^1$, $R^2$ and $R^3$ are each independently selected from hydrogen, $C_{1-6}$alkyl, hydroxy, halo and the like; $Alk^1$ and $Alk^2$ are optionally substituted $C_{1-6}$alkanediyl; $R^5$ is a radical of formula

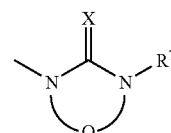

(d-1)

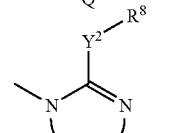

(d-2)

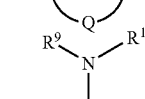

(d-3)

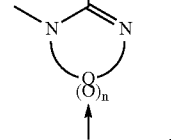

(d-4)

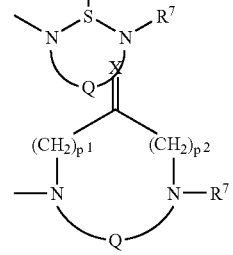

(d-5)

wherein n is 1 or 2; $p^1$ is 0, and $p^2$ is 1 or 2; or $p^1$ is 1 or 2, and $p^2$ is 0; X is oxygen, sulfur or $=NR^9$; $Y^2$ is oxygen or sulfur; $R^7$ is hydrogen, $C_{1-6}$alkyl, $C_{3-6}$cycloalkyl, phenyl or phenylmethyl; $R^8$ is $C_{1-6}$alkyl, $C_{3-6}$cycloalkyl phenyl or phenylmethyl; $R^9$ is cyano, $C_{1-6}$alkyl, $C_{3-6}$cycloalkyl, $C_{1-6}$alkyloxycarbonyl or aminocarbonyl; $R^{10}$ is hydrogen or $C_{1-6}$alkyl; and Q is a bivalent radical. Processes for preparing said products, formulations comprising said products and their use as a medicine are disclosed, in particular for treating conditions which are related to disturbed fundic accomodation.

2 Claims, No Drawings

FOREIGN PATENT DOCUMENTS

| | | |
|---|---|---|
| EP | 0 559 285 | 8/1993 |
| GB | 2019837 A | 11/1979 |
| WO | 93/17017 A1 | 9/1993 |
| WO | 97/28157 A1 | 8/1997 |
| WO | 00/75136 A1 | 6/1999 |
| WO | 99/29687 A1 | 6/1999 |
| WO | 00/75137 A1 | 12/2000 |

\* cited by examiner

COMPOUNDS FOR TREATING FUNDIC DISACCOMODATION

This application is a divisional application of prior application Ser. No. 10/311,612, filed Jun. 12, 2003, now U.S. Pat. No. 7,081,453, which is the national stage of Application No. PCT/EP01/06749, filed Jun. 13, 2001 which application claims priority from EP 00202180.6, filed Jun. 22, 2000.

The present invention is concerned with novel compounds of formula (I) having fundic relaxation properties. The invention further relates to methods for preparing such compounds, pharmaceutical compositions comprising said compounds as well as the use as a medicine of said compounds to restore disturbed fundic accomodation.

DE-2,400,094, published on 18 Jul. 1974, discloses 1-[1-[2-(1,4-benzodioxan-2-yl)-2-hydroxyethyl]-4-piperidyl-2-benzimidazolinones possessing blood pressure lowering activity.

DE-2,852,945, published on 26 Jun. 1980, discloses benzodioaxanylhydroxyethyl-piperidylimidazolidinones having antihypertensive activity.

EP-0,004,358, published on 3 Oct. 1979, discloses N-oxacycloalkylalkylpiperidines useful as antidepressants and psychostimulants.

EP-0,048,218, published on 24 Mar. 1982, discloses N-oxides of N-oxacycloalkyl-alkylpiperidines having antidepressant activity.

WO-93/17017, published on 2 Sep. 1993, discloses [(benzodioxane, benzofuran or benzopyran)alkylamino]alkyl-substituted guanidine as selective vasoconstrictors useful to treat conditions related to vasodilatation such as, e.g., migraine, cluster headache and headache associated with vascular disorders.

WO-95/053837, published on 23 Feb. 1995, encompasses dihydrobenzopyran-pyrimidine derivatives also having vasoconstrictive activity.

WO-97/28157, published on 7 Aug. 1997, discloses aminomethylchroman derivatives as $\alpha_2$-adrenergic receptor antagonists useful in the treatment of degenerative neurological conditions.

The compounds of the present invention differ from the cited art-known compounds structurally, by the nature of the bivalent radical -$a^1$=$a^2$-$a^3$=$a^4$-, the $R^5$ substituent, and pharmacologically by the fact that, unexpectedly, these compounds have fundic relaxation properties. Furthermore, the compounds of the present invention have additional beneficial pharmacological properties in that they have little or no vasoconstrictor activity.

The present invention concerns compounds of formula (I)

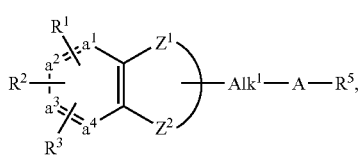

a stereochemically isomeric form thereof, an N-oxide form thereof, a pharmaceutically acceptable acid addition salt thereof, or a quaternary ammonium salt thereof, wherein -$a^1$=$a^2$-$a^3$=$a^4$- is a bivalent radical of formula

| | |
|---|---|
| —N=CH—CH=CH— | (a-1), |
| —CH=N—CH=CH— | (a-2), |
| —CH=CH—N=CH— | (a-3), |
| —CH=CH—CH=N— | (a-4), |
| —N=N—CH=CH— | (a-5), |
| —N=CH—N=CH— | (a-6), |
| —N=CH—CH=N— | (a-7), |
| —CH=N—N=CH— | (a-8), |
| —CH=N—CH=N— | (a-9), or |
| —CH=CH—N=N— | (a-10); |

-$Z^1$-$Z^2$- is a bivalent radical of formula

| | |
|---|---|
| —$Y^1$—CH($R^4$)—CH$_2$— | (b-1), |
| —$Y^1$—CH($R^4$)—O— | (b-2), |
| $Y^1$—CH($R^4$)—CH$_2$—O— | (b-3), |
| —$Y^1$—CH($R^4$)—CH$_2$—S— | (b-4), |
| —$Y^1$—CH($R^4$)—CH$_2$—NH— | (b-5), |
| —$Y^1$—C—CH($R^4$)—CH$_2$—CH$_2$— | (b-6), |
| —$Y^1$—CH($R^4$)—CH$_2$—CH$_2$—CH$_2$— | (b-7), |
| —$Y^1$—C($R^4$)=CH— | (b-8), |
| —$Y^1$—C($R^4$)=CH—CH$_2$— | (b-9), |
| —$Y^1$—CH($R^4$)—CH=CH— | (b-10), |
| —$Y^1$—C($R^4$)=CH—CH$_2$—CH$_2$— | (b-11), or |
| —$Y^1$—CH$_2$—CH($R^4$)C— | (b-12), | wherein, where possible, optionally one or two hydrogen atoms on the same or a different carbon or nitrogen atom may be replaced by hydroxy, $C_{1-4}$alkyloxy$C_{1-4}$alkyl, $C_{1-4}$alkylcarbonyl, or $C_{1-6}$alkyl optionally substituted with halo, hydroxy, $C_{3-6}$cycloalkyl, or phenyl;

$Y^1$ is oxygen or sulfur;

Alk$^1$ is $C_{1-4}$alkylcarbonyl, carbonyl$C_{1-4}$alkyl, $C_{1-4}$alkylcarbonyl$C_{1-4}$alkyl, carbonyl, or $C_{1-6}$alkanediyl optionally substituted with hydroxy, halo, amino, hydroxy$C_{1-4}$alkyl, $C_{1-4}$alkyloxy, hydroxycarbonyl, $C_{1-4}$alkyloxycarbonyl, aminocarbonyl, mono- or di($C_{1-4}$alkyl)aminocarbonyl, $C_{1-4}$alkyloxy$C_{1-4}$alkyl, $C_{1-4}$alkylcarbonyloxy, $C_{1-4}$alkylcarbonyloxy$C_{1-4}$alkyloxycarbonyloxy, $C_{1-4}$alkyloxyimino, phenyl$C_{1-4}$alkylamino, $C_{1-4}$alkyloxycarbonyl$C_{1-6}$alkenyl, cyano$C_{1-6}$alkenyl or $C_{1-6}$cycloalkylcarbonyloxy$C_{1-4}$alkyloxycarbonyloxy;

$R^1$, $R^2$ and $R^3$ are each independently selected from hydrogen, $C_{1-6}$alkyl, $C_{3-6}$alkenyl, $C_{1-6}$alkyloxy, hydroxycarbonyl, trihalomethyl, trihalomethoxy, halo, hydroxy, cyano, nitro, amino, $C_{1-6}$alkylcarbonylamino, $C_{1-6}$alkyloxycarbonyl, $C_{1-4}$alkylcarbonyloxy, aminocarbonyl, mono- or di($C_{1-6}$alkyl)aminocarbonyl, amino$C_{1-6}$alkyl, mono- or di($C_{1-6}$alkyl)amino$C_{1-6}$alkyl, $C_{1-4}$alkylcarbonyloxy$C_{1-4}$alkyloxycarbonyloxy, or $C_{3-6}$cycloalkylcarbonyloxy$C_{1-4}$alkyloxycarbonyloxy;

$R^4$ is hydrogen, hydroxycarbonyl, phenyl, aminocarbonyl, mono- or di($C_{1-4}$alkyl)aminocarbonyl, $C_{1-4}$alkyloxy$C_{1-4}$alkyl, $C_{1-4}$alkyloxycarbonyl, N-pyrolidinylcarbonyl, N-piperidinylcarbonyl, N-homopiperidinylcarbonyl, $C_{1-4}$alkylcarbonyloxy$C_{1-4}$alkyloxycarbonyl, $C_{1-4}$alkyloxycarbonylC$_{1-4}$alkyl, C$_{3-6}$cycloalkylcarbonyloxyC$_{1-4}$alkyloxycarbonyloxy, or C$_{1-6}$alkyl optionally substituted with hydroxy, cyano, amino, phenyl, mono- or di(C$_{1-4}$alkyl)amino, or mono- or di(C$_{1-4}$alkyl)aminocarbonyl;

-A- is a bivalent radical of formula

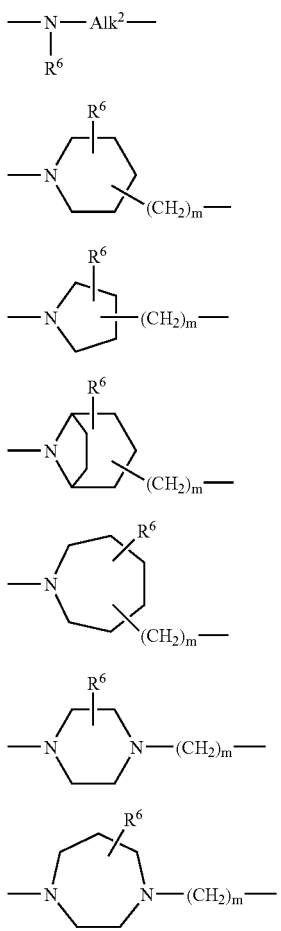

(c-1)
(c-2)
(c-3)
(c-4)
(c-5)
(c-6)
(c-7)

wherein m is 0 or 1;

Alk$^2$ is a bivalent radical independently selected from C$_{1-4}$alkylcarbonylC$_{1-4}$alkyl; phenyl; C$_{3-6}$cycloalkylcarbonyloxyC$_{1-4}$alkyloxycarbonyloxy; C$_{3-8}$cycloalkanediyl optionally substituted with one or more halo, hydroxy, hydroxycarbonyl, hydroxyC$_{1-4}$alkyl, C$_{1-4}$alkyloxy, C$_{1-4}$alkyloxyC$_{1-4}$alkyl, C$_{1-4}$alkyloxycarbonyl, C$_{1-4}$alkylcarbonyloxyC$_{1-4}$alkyloxycarbonyloxy, C$_{3-6}$cycloalkylcarbonyloxyC$_{1-4}$alkyloxycarbonyloxy, phenyl; or C$_{1-6}$alkyl optionally substituted with one or more hydroxy, halo, amino, hydroxycarbonyl, hydroxyC$_{1-4}$alkyl, C$_{1-4}$alkyloxy, C$_{1-4}$alkyloxyC$_{1-4}$alkyl, C$_{1-4}$alkyloxycarbonyl, C$_{1-4}$alkylcarbonyloxyC$_{1-4}$alkyloxycarbonyloxy, C$_{3-6}$cycloalkyl, aminocarbonyl, mono- or di(C$_{1-4}$alkyl)aminocarbonyl, or C$_{1-6}$alkyl wherein the C$_{1-6}$alkyl together with the carbon atom to which it is attached may form a C$_{3-6}$cycloalkyl;

R$^6$ is hydrogen, C$_{1-4}$alkyl, halo, hydroxy, hydroxyC$_{1-4}$alkyl, C$_{1-4}$alkyloxy, aminoC$_{1-4}$alkyl, C$_{1-4}$alkyloxycarbonyl, C$_{1-4}$alkylcarbonyloxyC$_{1-4}$alkyloxycarbonyl, amino, hydroxycarbonyl, aminocarbonyl, mono- or di(C$_{1-4}$alkyl)aminocarbonyl, or C$_{3-6}$cycloalkylcarbonyloxyC$_{1-4}$alkyloxycarbonyloxy;

R$^5$ is a radical of formula

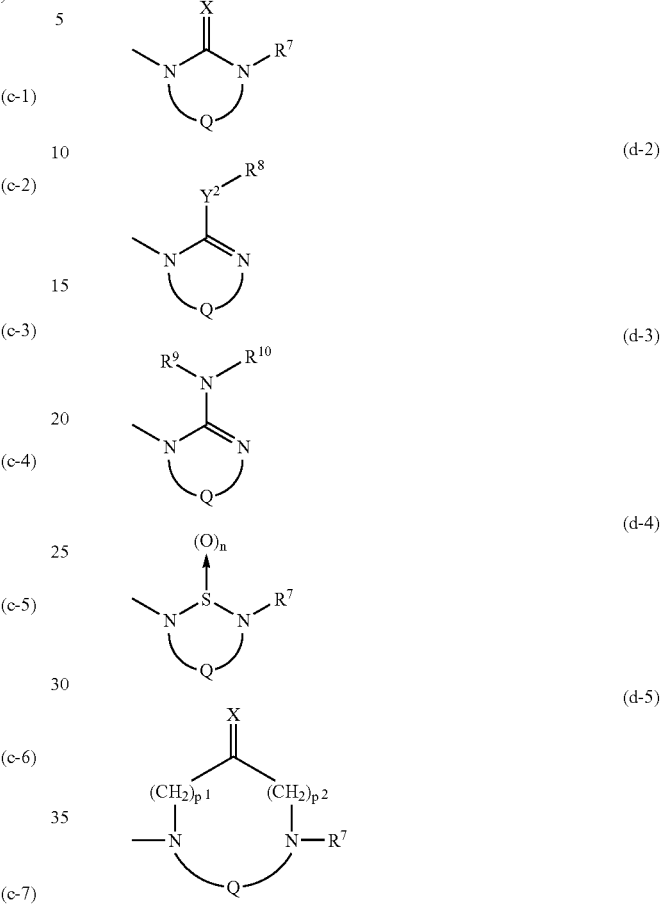

(d-1)
(d-2)
(d-3)
(d-4)
(d-5)

wherein n is 1 or 2;

p$^1$ is 0, and p$^2$ is 1 or 2; or p$^1$ is 1 or 2, and p$^2$ is 0;

X is oxygen, sulfur, NR$^9$ or CHNO$_2$;

Y$^2$ is oxygen or sulfur;

R$^7$ is hydrogen, C$_{1-6}$alkyl, C$_{3-6}$cycloalkyl, phenyl or phenylmethyl;

R$^8$ is C$_{1-6}$alkyl, C$_{3-6}$cycloalkyl, phenyl or phenylmethyl;

R$^9$ is cyano, C$_{1-6}$alkyl, C$_{3-6}$cycloalkyl, C$_{1-6}$alkyloxycarbonyl or aminocarbonyl;

R$^{10}$ is hydrogen or C$_{1-6}$alkyl;

or R$^9$ and R$^{10}$ taken together with the nitrogen atom to which they are attached may form a pyrrolidinyl, piperidinyl, homopiperidinyl, piperazinyl, or morpholinyl group, optionally substituted with C$_{1-4}$alkyl or C$_{1-4}$alkyloxy; and Q is a bivalent radical of formula —CH$_2$—CH$_2$— (e-1), —CH$_2$—CH$_2$—CH$_2$— (e-2), —CH$_2$—CH$_2$—CH$_2$—CH$_2$— (e-3), —CH=CH— (e-4), —CH$_2$—CO— (e-5), —CO—CH$_2$— (e-6), —(CH$_2$)$_2$—CO— (e-7), —CO—(CH$_2$)$_2$—                    (e-8), —CO—CH$_2$—CO—                    (e-9), —CH$_2$—CO—CH$_2$—               (e-10), wherein optionally one or two hydrogen atoms on the same or a different carbon atom may be replaced by C$_{1-4}$alkyl, hydroxy or phenyl, or Q is a bivalent radical of formula

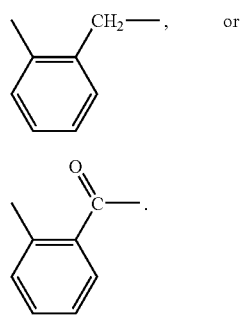

(e-11)

(e-12)

As used in the foregoing definitions halo is generic to fluoro, chloro, bromo and iodo; C$_{1-4}$alkyl defines straight and branched chain saturated hydrocarbon radicals having from 1 to 4 carbon atoms such as, for example, methyl, ethyl, propyl, butyl, 1-methyl-ethyl, 2-methylpropyl and the like; C$_{1-6}$alkyl is meant to include C$_{1-4}$alkyl and the higher homologues thereof having 5 or 6 carbon atoms, such as, for example, 2-methyl-butyl, pentyl, hexyl and the like; C$_{3-6}$cycloalkyl is generic to cyclopropyl, cyclobutyl, cyclopentyl and cyclohexyl; C$_{3-6}$alkenyl defines straight and branched chain unsaturated hydrocarbon radicals having from 3 to 6 carbon atoms, such as propenyl, butenyl, pentenyl or hexenyl; C$_{1-2}$alkanediyl defines methylene or 1,2-ethanediyl; C$_{1-3}$alkanediyl defines bivalent straight or branched chain hydrocarbon radicals containing from 1 to 3 carbon atoms such as, for example, methylene, 1,2-ethanediyl, 1,3-propanediyl, and the branched isomers thereof; C$_{1-5}$alkanediyl defines bivalent straight or branched chain hydrocarbon radicals containing from 1 to 5 carbon atoms such as, for example, methylene, 1,2-ethanediyl, 1,3-propanediyl, 1,4-butanediyl, 1,5-pentanediyl, and the branched isomers thereof; C$_{1-6}$alkanediyl includes C$_{1-5}$alkanediyl and the higher homologues thereof having 6 carbon atoms such as, for example, 1,6-hexanediyl and the like. The term "CO" refers to a carbonyl group.

Some examples of the R$^5$ moiety are:

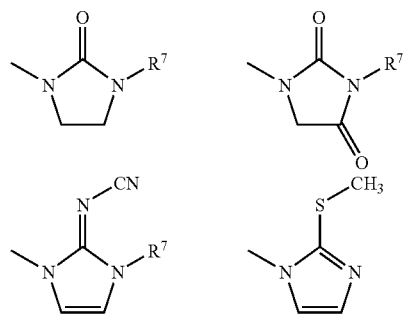

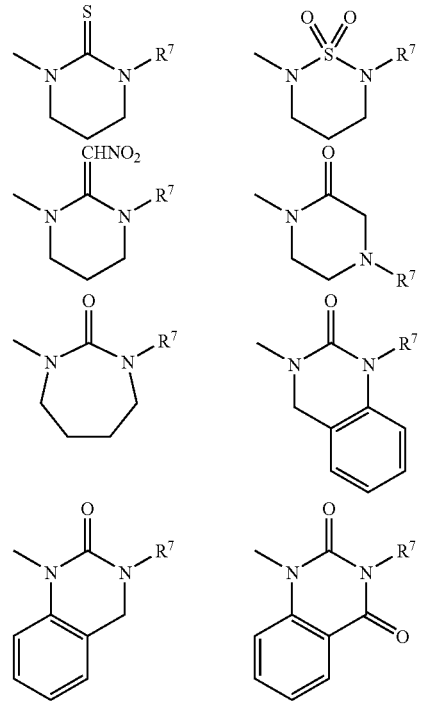

The term "stereochemically isomeric forms" as used hereinbefore defines all the possible isomeric forms which the compounds of formula (I) may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration; substituents on bivalent cyclic (partially) saturated radicals may have either the cis- or trans-configuration. Compounds encompassing double bonds can have an E or Z-stereochemistry at said double bond. Stereochemically isomeric forms of the compounds of formula (I) are obviously intended to be embraced within the scope of this invention.

The pharmaceutically acceptable acid addition salts as mentioned hereinabove are meant to comprise the therapeutically active non-toxic acid addition salt forms which the compounds of formula (I) are able to form. The pharmaceutically acceptable acid addition salts can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

Quaternary ammonium salts of compounds of formula (I) as used herein defines which the compounds of formula (I) are able to form by reaction between a basic nitrogen of a compound of formula (I) and an appropriate quaternizing agent, such as, for example, an optionally substituted alkylhalide, arylhalide or arylalkylhalide, e.g. methyliodide or benzyliodide. Other reactants with good leaving groups may also be used, such as alkyl trifluoromethanesulfonates, alkyl methanesulfonates, and alkyl p-toluenesulfonates. A quaternary ammonium salt has a positively charged nitrogen. Pharmaceutically acceptable counterions include chloro, bromo, iodo, trifluoroacetate and acetate. The counterion of choice can be made using ion exchange resin columns.

The term addition salt as used hereinabove also comprises the solvates which the compounds of formula (I) as well as the salts thereof, are able to form. Such solvates are for example hydrates, alcoholates and the like.

The N-oxide forms of the compounds of formula (I), which may be prepared in art-known manners, are meant to comprise those compounds of formula (I) wherein a nitrogen atom is oxidized to the N-oxide.

The absolute stereochemical configuration of some compounds of formula (I) and of intermediates used in their preparation, was not experimentally determined. In those cases the stereochemically isomeric form which was first isolated is designated as "A" and the second as "B", without further reference to the actual stereochemical configuration. However, said "A" and "B" isomeric forms can be unambiguously characterized by for instance their optical rotation in case "A" and "B" have an enantiomeric relationship. A person skilled in the art is able to determine the absolute configuration of such compounds using art-known methods, e.g. X-ray diffraction.

A first group of compounds are those compounds of formula (I) wherein the bivalent radical $-Z^1-Z^2$ is of formula (b-1), (b-2), (b-3), (b-4), (b-5), (b-6), (b-7), (b-8), (b-9), (b-10), or (b-1).

Interesting compounds are those compounds of formula (I) wherein one or more of the following restrictions apply:
a) the bivalent radical $-Z^1-Z^2$- is of formula (b-1), or (b-2); or
b) the bivalent radical $-Z^1-Z^2$- is of formula (b-2), (b-3), (b-4), or (b-5); in particular the bivalent radical $-Z^1-Z^2$- is of formula (b-2) or (b-3); or
c) the bivalent radical $-Z^1-Z^2$- is of formula (b-3);
d) the bivalent radical $-a^1=a^2-a^3=a^4$- is of formula (a-1), (a-2) or (a-4); in particular $-a^1=a^2-a^3=a^4$- is of formula (a-1);
e) the bivalent radical -A- is of formula (c-1) or (c-2);
f) $R^1$, $R^2$ and $R^3$ are each independently selected from hydrogen, $C_{1-6}$alkyl, hydroxy or halo;
g) $R^4$ is hydrogen;
h) $Alk^1$ is $C_{1-2}$alkanediyl optionally substituted with hydroxy, in particular $Alk^1$ is $-CH_2-$;
i) $Alk^2$ is $C_{1-3}$alkanediyl optionally substituted with hydroxy, in particular $Alk^2$ is $-(CH_2)_3-$ or $-CH_2-CHOH-CH_2-$; and/or
j) $R^6$ is hydrogen of phenylmethyl.

Particular compounds of formula (I) are those compounds of formula (I) wherein the bivalent radical $-Z^1-Z^2$- is of formula $-O-CH_2-CH_2-O-$ and the bivalent radical $-a^1=a^2-a^3=a^4$- is of formula (a-1).

Other particular compounds are those compounds of formula (I) wherein the bivalent radical $-Z^1-Z^2$- is of formula $-O-CH_2-O-$ and the bivalent radical $-a^1=a^2-a^3=a^4$- is of formula (a-1).

Preferred compounds are those compounds of formula (I) wherein $R^5$ is a radical of formula (d-1) wherein X is oxygen, $R^7$ is hydrogen, and Q is (e-2)

More preferred compounds are those compounds of formula (I) wherein the bivalent radical $-a^1=a^2-a^3=a^4$- is of formula (a-1), (a-2) or (a-4); the bivalen radical $-Z^1-Z^2$- is of formula (b-1), (b-2) or (b-4) wherein $R^4$ is hydrogen; $Alk^1$ is $-CH_2-$; the bivalent radical -A- is of formula (c-1) or (c-2); and $R^5$ is a radical of formula (d-1) wherein X is oxygen, $R^7$ is hydrogen, and Q is (e-1), (e-2), (e-5) or (e-7).

Other more preferred compounds are those compounds of formula (I) wherein the bivalent radical $-a^1=a^2-a^3=a^4$- is of formula (a-1), (a-2) or (a-4); the bivalent radical $-Z^1-Z^2$- is of formula (b-1), (b-2) or (b-4) wherein $R^4$ is hydrogen; $Alk^1$ is $-CH_2-$; the bivalent radical -A- is of formula (c-2) wherein $R^6$ is hydroxymethyl; and $R^5$ is a radical of formula (d-1) wherein X is oxygen, $R^7$ is hydrogen, and Q is (e-1), (e-2), (e-5) or (e-7).

Still other more preferred compounds are those compounds of formula (I) wherein the bivalent radical $-a^1=a^2-a^3=a^4$- is of formula (a-1), (a-2) or (a-4); the bivalent radical $-Z^1-Z^2$- is of formula (b-1), (b-2) or (b-4) wherein $R^4$ is hydrogen; $Alk^1$ is $-CH_2-$; the bivalent radical -A- is of formula $-CH_2-CHOH-CH_2-$; and $R^5$ is a radical of formula (d-1) wherein X is oxygen, $R^7$ is hydrogen, and Q is (e-1), (e-2), (e-5) or (e-7).

Most preferred compounds are those compounds of formula (I) wherein the bivalent radical $-a^1=a^2-a^3=a^4$- is of formula (a-1); the bivalent radical $-Z^1-Z^2$- is of formula (b-3) wherein $Y^1$ is O and $R^4$ is hydrogen; the bivalent radical $Alk^1$ is $-CH_2-$; the bivalent radical A is of formula (c-2) wherein m is the integer 0; and radical $R^5$ is of formula (d-1) wherein the bivalent radical Q is of formula (e-1) or (e-2).

Other most preferred compounds are those compounds of formula (I) wherein the bivalent radical $-a^1=a^2-a^3=a^4$- is of formula (a-1); the bivalent radical $-Z^1-Z^2$- is of formula (b-3) wherein $Y^1$ is O and $R^4$ is hydrogen; the bivalent radical $Alk^1$ is $-CH_2-$; the bivalent radical A is of formula (c-1) wherein $Alk^2$ is $-(CH_2)_3-$; and radical $R^5$ is of formula (d-1) wherein the bivalent radical Q is of formula (e-5) or (e-7).

Preferable compounds are

1-[1-[(2,3-dihydro[1,4]dioxino[2,3-b]pyridin-3-yl)methyl]-4-piperidinyl]-2-imidazolidinone;

1-[1-[(2,3-dihydro[1,4]dioxino[2,3-b]pyridin-3-yl)methyl]-4-piperidinyl]tetrahydro-2(1H)-pyrimidinone;

1-[3-[[(2,3-dihydro[1,4]dioxino[2,3-b]pyridin-3-yl)methyl]amino]propyl]dihydro-2,4(1H,3H)-pyrimidinedione; and 1-[3-[[(2,3-dihydro[1,4]dioxino[2,3-b]pyridin-3-yl)methyl]amino]propyl]-2,4-imidazolidinedione, a pharmaceutically acceptable acid addition salt, a stereochemically isomeric form, or an N-oxide form thereof. In particular, the (S)-stereoisomers of the above four compounds are preferred.

The compounds of the present invention can generally be prepared by alkylating an intermediate of formula (III) with an intermediate of formula (II), wherein W is an appropriate leaving group such as, for example, halo, e.g. fluoro, chloro, bromo, iodo, or in some instances W may also be a sulfonyloxy group, e.g. methanesulfonyloxy, benzenesulfonyloxy, trifluoromethanesulfonyloxy and the like reactive leaving groups. The reaction can be performed in a reaction-inert solvent such as, for example, acetonitrile or tetrahydrofuran, and optionally in the presence of a suitable base such as, for example, sodium carbonate, potassium carbonate, calciumoxide or triethylamine. Stirring may enhance the rate of the reaction. The reaction may conveniently be carried out at a temperature ranging between room temperature and the reflux temperature of the reaction mixture and, if desired, the reaction may be carried out in an autoclave at an increased pressure.

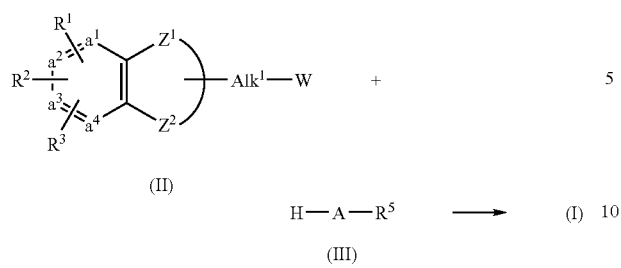

(II)

H—A—R⁵ → (I)

(III)

Compounds of formula (I) can also be prepared by reductively alkylating an intermediate of formula (IV), wherein Alk¹ represents a direct bond or $C_{1-5}$alkanediyl, following art-known reductive alkylation procedures with an intermediate of formula (III).

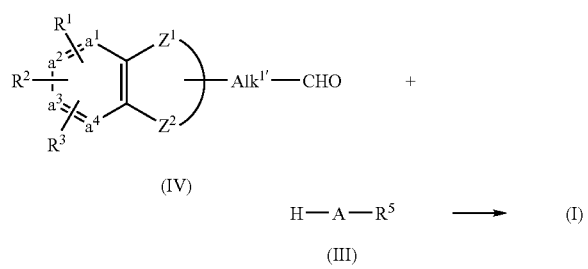

(IV)

H—A—R⁵ → (I)

(III)

Said reductive alkylation can be performed in a reaction-inert solvent such as, for example, dichloromethane, ethanol, toluene or a mixture thereof, and in the presence of a reducing agent such as, for example, a borohydride, e.g. sodium borohydride, sodium cyanoborohydride or triacetoxy borohydride. It may also be convenient to use hydrogen as a reducing agent in combination with a suitable catalyst such as, for example, palladium-on-charcoal, rhodium-on-carbon or platinum-on-charcoal. In case hydrogen is used as reducing agent, it may be advantageous to add a dehydrating agent to the reaction mixture such as, for example, aluminium tert-butoxide. In order to prevent the undesired further hydrogenation of certain functional groups in the reactants and the reaction products, it may also be advantageous to add an appropriate catalyst-poison to the reaction mixture, e.g., thiophene or quinoline-sulphur. To enhance the rate of the reaction, the temperature may be elevated in a range between room temperature and the reflux temperature of the reaction mixture and optionally the pressure of the hydrogen gas may be raised.

Alternatively, compounds of formula (I) can also be prepared by reacting an acid chloride of formula (V), wherein Alk¹' represents $C_{1-5}$alkanediyl or a direct bond, with an intermediate of formula (III) under suitable reaction conditions.

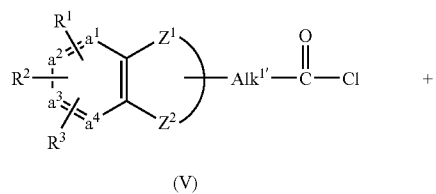

(V)

-continued

H—A—R⁵ → (I)

(III)

Said reaction can be performed under hydrogenation conditions with hydrogen gas in the presence of a suitable catalyst such as, for example, palladium-on-charcoal, rhodium-on-carbon or platinum-on-charcoal, in a suitable solvent such as, for example, ethyl acetate, and in the presence of magnesiumoxide. In order to prevent the undesired further hydrogenation of certain functional groups in the reactants and the reaction products, it may also be advantageous to add an appropriate catalyst-poison to the reaction mixture, e.g. thiophene or quinoline-sulphur. To enhance the rate of the reaction, the temperature may be elevated in a range between room temperature and the reflux temperature of the reaction mixture and optionally the pressure of the hydrogen gas may be raised.

Compounds of formula (I-a), defined as compounds of formula (I) wherein the bivalent radical -A- represents —NR⁶—CH₂—CH(OH)—CH₂—, can be prepared by reacting intermediates of formula (VI) with intermediates of formula (VII) in a reaction-inert solvent, such as methanol, and optionally in the presence of an anorganic base, such as sodium carbonate.

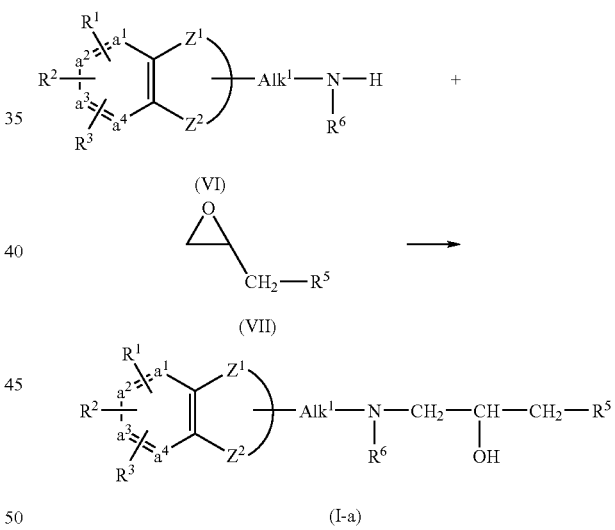

The compounds of formula (I) may further be prepared by converting compounds of formula (I) into each other according to art-known group transformation reactions. For instance, compounds of formula (I) wherein R⁶ is phenylmethyl can be converted to the corresponding compounds of formula (I) wherein R⁶ is hydrogen by art-known debenzylation procedures. Said debenzylation can be performed following art-known procedures such as catalytic hydrogenation using appropriate catalysts, e.g. platinum on charcoal, palladium on charcoal, in appropriate solvents such as methanol, ethanol, 2-propanol, diethyl ether, tetrahydrofuran, and the like. Furthermore, compounds of formula (I) wherein R⁶ is hydrogen may be alkylated using art-known procedures such as, e.g. reductive N-alkylation with a suitable aldehyde or ketone.

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarbo-peroxoic acid or halo substituted benzenecarboperoxoic acid, e.g. 3-chlorobenzene-carboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

The starting materials and some of the intermediates are known compounds and are commercially available or may be prepared according to conventional reaction procedures generally known in the art. For example, some intermediates of formula (III) can be prepared as described in Examples A.4 and A.5 of WO-99/29687.

Compounds of formula (I) and some of the intermediates may have one or more stereogenic centers in their structure, present in a R or a S configuration, such as, e.g. the carbon atom bearing the $R^4$ substituent, and the carbon atom linked to the -$Alk^1$-A-$R^5$ moiety.

The compounds of formula (I) as prepared in the hereinabove described processes may be synthesized in the form of racemic mixtures of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of formula (I), the N-oxide forms, the pharmaceutically acceptable salts and stereoisomeric forms thereof possess favourable fundic relaxation properties as evidenced in pharmacological example C-1, the "Gastric tone measured by an electronic barostat in conscious dogs"-test.

Furthermore, the compounds of the present invention have additional beneficial pharmacological properties in that they have little or no vasoconstrictor activity as can be demonstrated in pharmacological example C.2 "Vasoconstrictive activity on basilar artery". Vasconstrictor activity can cause undesirable side-effects such as coronary effects which can induce chest pain. In addition, the compounds of the present invention have other favourable pharmacokinetic properties in that they have a fast onset and short duration of action, in absence of any $CYP_{450}$ 2D6 or 3A4 mediated metabolism.

During the consumption of a meal the fundus, i.e. the proximal part of the stomach, relaxes and provides a "reservoir" function. Patients having a disturbed or an impaired adaptive relaxation of the fundus upon food ingestion have been shown to be hypersensitive to gastric distension and display dyspeptic symptoms. Therefore, it is believed that compounds which are able to normalize or restore a disturbed fundic accomodation are useful to relieve patients suffering from said dyspeptic symptoms.

In view of the capability of the compounds of the present invention to relax the fundus, the subject compounds are useful to treat disorders or conditions related to a disturbed, hampered or impaired accomodation of the fundus such as, e.g. dyspepsia, early satiety, bloating and anorexia.

Dyspepsia is described as a motility disorder. Symptoms can be caused by a delayed gastric emptying or by impaired relaxation of the fundus to food ingestion. Warm-blooded animals, including humans, (generally called herein patients) suffering from dyspeptic symptoms as a result of delayed gastric emptying usually have a normal fundic relaxation and can be relieved of their dyspeptic symptoms by administering a prokinetic agent such as, e.g. cisapride. Patients can have dyspeptic symptoms without having a disturbed gastric emptying. Their dyspeptic symptoms may result from a hypercontracted fundus or hypersensitivity resulting in a diminished compliance and abnormalities in the adaptive fundic relaxation. A hypercontracted fundus results in a diminished compliance of the stomach. The "compliance of the stomach" can be expressed as the ratio of the volume of the stomach over the pressure exerted by the stomach wall. The compliance of the stomach relates to the gastric tone, which is the result of the tonic contraction of muscle fibers of the proximal stomach. This proximal part of the stomach, by exerting a regulated tonic contraction (gastric tone), accomplishes the reservoir function of the stomach.

Patients suffering from early satiety cannot finish a normal meal since they feel saturated before they are able to finish said normal meal. Normally when a subject starts eating, the stomach will show an adaptive relaxation, i.e. the stomach will relax to accept the food that is ingested. This adaptive relaxation is not possible when the compliance of the stomach is hampered which results in an impaired relaxation of the fundus.

In view of the utility of the compounds of formula (I), it follows that the present invention also provides a method of treating warm-blooded animals, including humans, (generally called herein patients) suffering from disturbed, hampered or impaired accomodation of the fundus to food ingestion. Consequently a method of treatment is provided for relieving patients suffering from conditions, such as, for example, dyspepsia, early satiety, bloating and anorexia.

Hence, the use of a compound of formula (I) as a medicine is provided, and in particular the use of a compound of formula (I) for the manufacture of a medicine for treating conditions involving an disturbed, hampered or impaired accomodation of the fundus to food ingestion. Both prophylactic and therapeutic treatment are envisaged.

The symptoms of impaired fundic relaxation may also arise due to the intake of chemical substances, e.g. Selective Seretonine Re-uptake Inhibitors (SSRI's), such as fluoxetine, paroxetine, fluvoxamine, citalopram and sertraline.

To prepare the pharmaceutical compositions of this invention, an effective amount of the particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions. These compositions may be administered in various ways, e.g., as a transdermal patch, as a spot-on, as an ointment. Acid addition salts of (I) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

For oral administration, the pharmaceutical compositions may take the form of solid dose forms, for example, tablets (both swallowable-only and chewable forms), capsules or gelcaps, prepared by conventional means with pharmaceutically acceptable excipients such as binding agents (e.g. pregelatinised maize starch, polyvinylpyrrolidone or hydroxypropyl methylcellulose); fillers (e.g. lactose, microcrystalline cellulose or calcium phosphate); lubricants e.g. magnesium stearate, talc or silica); disintegrants (e.g. potato starch or sodium starch glycollate); or wetting agents (e.g. sodium lauryl sulphate). The tablets may be coated by methods well known in the art.

Liquid preparations for oral administration may take the form of, for example, solutions, syrups or suspensions, or they may be presented as a dry product for constitution with water or other suitable vehicle before use. Such liquid preparations may be prepared by conventional means, optionally with pharmaceutically acceptable additives such as suspending agents (e.g. sorbitol syrup, methylcellulose, hydroxypropyl methylcellulose or hydrogenated edible fats); emulsifying agents (e.g. lecithin or acacia); non-aqueous vehicles (e.g. almond oil, oily esters or ethyl alcohol); and preservatives (e.g. methyl or propyl p-hydroxybenzoates or sorbic acid).

Pharmaceutically acceptable sweeteners comprise preferably at least one intense sweetener such as saccharin, sodium or calcium saccharin, aspartame, acesulfame potassium, sodium cyclamate, alitame, a dihydrochalcone sweetener, monellin, stevioside or sucralose (4,1',6'-trichloro-4,1',6'-trideoxygalactosucrose), preferably saccharin, sodium or calcium saccharin, and optionally a bulk sweetener such as sorbitol, mannitol, fructose, sucrose, maltose, isomalt, glucose, hydrogenated glucose syrup, xylitol, caramel or honey.

Intense sweeteners are conveniently employed in low concentrations. For example, in the case of sodium saccharin, the concentration may range from 0.04% to 0.1% (w/v) based on the total volume of the final formulation, and preferably is about 0.06% in the low-dosage formulations and about 0.08% in the high-dosage ones. The bulk sweetener can effectively be used in larger quantities ranging from about 10% to about 35%, preferably from about 10% to 15% (w/v).

The pharmaceutically acceptable flavours which can mask the bitter tasting ingredients in the low-dosage formulations are preferably fruit flavours such as cherry, raspberry, black currant or strawberry flavour. A combination of two flavours may yield very good results. In the high-dosage formulations stronger flavours may be required such as Caramel Chocolate flavour, Mint Cool flavour, Fantasy flavour and the like pharmaceutically acceptable strong flavours. Each flavour may be present in the final composition in a concentration ranging from 0.05% to 1% (w/v). Combinations of said strong flavours are advantageously used. Preferably a flavour is used that does not undergo any change or loss of taste and colour under the acidic conditions of the formulation.

The compounds of the invention may also be formulated as depot preparations. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example as a sparingly soluble salt.

The compounds of the invention may be formulated for parenteral administration by injection, conveniently intravenous, intramuscular or subcutaneous injection, for example by bolus injection or continuous intravenous infusion. Formulations for injection may be presented in unit dosage form e.g. in ampoules or in multidose containers, with an added preservative. The compositions may take such forms as suspensions, solutions or emulsions in oily or aqueous vehicles, and may contain formulatory agents such as isotonizing, suspending, stabilising and/or dispersing agents. Alternatively, the active ingredient may be in powder form for constitution with a suitable vehicle, e.g. sterile pyrogen-free water before use.

The compounds of the invention may also be formulated in rectal compositions such as suppositories or retention enemas, e.g. containing conventional suppository bases such as cocoa butter or other glycerides.

For intranasal administration the compounds of the invention may be used, for example, as a liquid spray, as a powder or in the form of drops.

The formulations of the present invention may optionally include an anti-flatulent, such as simethicone, alpha-D-galactosidase and the like.

In general it is contemplated that a therapeutically effective amount would be from about 0.001 mg/kg to about 2 mg/kg body weight, preferably from about 0.02 mg/kg to about 0.5 mg/kg body weight. A method of treatment may also include administering the active ingredient on a regimen of between two or four intakes per day.

EXPERIMENTAL PART

In the procedures described hereinafter the following abbreviations were used: "ACN" stands for acetonitrile and "DCM" stands for dichloromethane.

For some chemicals the chemical formula was used, e.g. $CH_2Cl_2$ for dichloromethane, $CH_3OH$ for methanol, $NH_3$ for ammonia, HCl for hydrochloric acid, and NaOH for sodium hydroxide.

In those cases the stereochemically isomeric form which was first isolated is designated as "A", the second as "B", the third one as "C" and the fourth one as "D", without further reference to the actual stereochemical configuration.

A. Preparation of the Intermediates

EXAMPLE A.1

Methanesulfonyl chloride (0.012 mol) in DCM (6 ml) was added dropwise to a mixture, cooled on an ice bath, of 2,3-dihydro-1,4-dioxino[2,3-b]pyridine-3-methanol (0.008 mol) and triethylamine (0.016 mol) in DCM (26 ml) and the mixture was stirred at 5° C. for 1 hour. The mixture was filtered off, the filtrate was washed with water and extracted. The organic layer was dried, filtered off and evaporated till dryness. The product was used without further purification, yielding 2.17 g of (±)-2,3-dihydro-1,4-dioxino[2,3-b]pyridine-3-methanolmethanesulfonate (ester) (intermediate 1).

EXAMPLE A.2 a) A mixture of 2,3-dihydro-3-[(phenylmethoxy)methyl]-1,4-dioxino[2,3-b]pyridine (0.0638 mol) in $CH_3OH$ (250 ml) was hydrogenated with palladium-on-carbon (10%, 2 g) as a catalyst. After uptake of hydrogen (1 equivalent), the catalyst was filtered off and the filtrate was evaporated. This fraction was purified by HPLC (eluent ethanol/methanol 60/40; column: Chiralpak AD 20 μm). Two fractions were collected and the solvent was evaporated, yielding 4.06 g of (S)-2,3-dihydro-1,4-dioxino[2,3-b]-pyridine-3-methanol (intermediate 2-a) ($[\alpha]_D^{20}$=−34.33°; c=25.34 mg/5 ml in methanol) and 3.81 g of (R)-2,3-dihydro-1,4-dioxino[2,3-b]-pyridine-3-methanol (intermediate 2-b) ($[\alpha]_D^{20}$=+32.740; c=22.60 mg/5 ml in methanol).

b) A mixture of intermediate (2-a) (0.023 mol) and triethylamine (0.046 mol) in DCM (40 ml) was stirred at 0° C. A mixture of methanesulfonyl chloride (0.035 mol) in DCM (10 ml) was added dropwise. The mixture was stirred on an ice bath for 2 hours and then washed with $H_2O$/NaCl. The organic layer was dried, filtered and the solvent was evaporated. The residue (oil) was solidified in DIPE. The precipitate was filtered off and dried, yielding 5 g of (S)-2,3-dihydro-1,4-dioxino[2,3-b]pyridine-3-methanol methanesulfonate (ester) (intermediate 3) ($[\alpha]_D^{20}$−27.89°; c=25.10 mg/5 ml in methanol; mp. 136° C.).

EXAMPLE A.3 a) Reaction under a nitrogen atmosphere. NaH 60% (0.4725 mol) was stirred in DMF (225 ml). 2,3-Pyridinediol (0.225 mol) was added portionwise and the mixture was stirred for 30 minutes at room temperature. The reaction mixture was cooled in an ice-water bath and 1,1-dichloro-2-methoxy-2-oxo-ethyl (1.125 mol) was added dropwise. The resulting reaction mixture was stirred for 5 hours at 95° C., then stirred overnight at room temperature. The cooled crude reaction mixture was treated with water, filtered over Celite and extracted with ethyl acetate. The separated organic layer was dried, filtered and the solvent was evaporated. The residue was purified by short open column chromatography over silica gel (eluent: DCM). The desired fractions were collected and the solvent was evaporated, yielding 4.13 g of (±)-methyl 1,3-dioxolo[4,5-b]pyridine-2-carboxylate (intermediate 4).

b) Reaction under a nitrogen atmosphere. A solution of intermediate (4) (0.042 mol) in THF (48 ml) was added dropwise to $LiAlH_4$ (1 Min THF) (0.0466 mol) and cooled with an ice-water bath. The resulting reaction mixture was stirred for one hour at room temperature. The reaction mixture was treated carefully with a 10% $NH_4Cl$ solution and it was diluted with water and ethyl acetate. The reaction mixture was filtered over Celite and the filtrate was extracted. The separated organic layer was dried, filtered and the solvent was evaporated. The residue was washed with DCM, filtered off and dried, yielding 2.78 g of (±)-1,3-dioxolo[4,5-b]pyridine-2-methanol (intermediate 5).

c) A solution of intermediate (5) (0.018 mol) and triethyl amine (0.036 mol) in DCM (80 ml) was stirred and cooled with an ice-water bath. Methanesulfonyl chloride (0.027 mol) was added dropwise and the resulting reaction mixture was stirred for one hour while cooling on an ice-bath. The crude reaction mixture was washed with water and brine, then extracted. The separated organic layer was dried, filtered and the solvent was evaporated, yielding 4.2 g of (±)-1,3-dioxolo[4,5-b]pyridine-2-methanol methanesulfonate (ester) (intermediate 6).

EXAMPLE A.4 a) Under nitrogen atmosphere. 2-propen-1-ol (0.002 mol) was added dropwise to a stirred mixture of NaH 60% (0.002 mol) in DME (5 ml). The mixture was stirred at room temperature for 15 minutes. A solution of 3-(methoxymethoxy)-4-chloropyridine (0.0017 mol) in DME (5 ml) was added dropwise. The resulting reaction mixture was stirred at reflux overnight. The mixture was washed with water and extracted with ethyl acetate. The organic layer was dried, filtered and evaporated till dryness. The residue was purified by open column chromatography (eluent: hexane/ethyl acetate 3/2; $CH_2Cl_2$/2-propanone 90/10; $CH_2Cl_2$/MeOH 96/4). The product fractions were collected and the solvent was evaporated, yielding 0.18 g of 3-(methoxymethoxy)-4-(2-propenyloxy)pyridine (intermediate 7).

b) Bromine (0.00092 mol) was added dropwise to a solution of intermediate (7) (0.00092 mol) in DCM (2 ml). The reaction mixture was stirred at room temperature for 15 minutes. The mixture was poured into a saturated $NaHCO_3$ solution with a few drops of a 10% $Na_2SO_4$ solution. This mixture was extracted. The organic layer was dried over $Na_2SO_4$, filtered and evaporated till dryness, yielding 0.32 g of (±)-4-(2,3-dibromopropoxy)-3-(methoxymethoxy) pyridine (intermediate 8).

c) A mixture of intermediate (8) (0.0248 mol), HCl (35.42 ml) and ethanol (40 ml) was stirred at room temperature overnight. The reaction mixture was concentrated under vacuum. The concentrate was cooled on an ice-water bath. The mixture was neutralized with a saturated $NaHCO_3$ solution and extracted with ethyl acetate. The organic layer was dried, filtered and evaporated till dryness. The residue was purified by open column chromatography (eluent: $CH_2Cl_2$; $CH_2Cl_2$/MeOH (98/2, 96/4 and 90/10)). The pure fractions were collected and the solvent was evaporated, yielding 4.27 g of (±)-4-(2,3-dibromopropoxy)-3-pyridinol (intermediate 9).

d) A solution of intermediate (9) (0.0097 mol) in ethanol (50 ml) was stirred and refluxed overnight. NaHCO$_3$ (0.0097 mol) was added and the resulting reaction mixture was stirred and refluxed overnight. The solvent was evaporated. The residue was washed with water and extracted with DCM. The organic layer was dried, filtered and the solvent was evaporated. The residue was purified by open column chromatography (eluent: hexane/ethyl acetate (3/2)). The pure fractions were collected and the solvent was evaporated, yielding 1.51 g of (±)-3-(bromomethyl)-2,3-dihydro-1,4-dioxino[2,3-c]pyridine (intermediate 10).

EXAMPLE A.5 a) A mixture of 2,2 dimethyl-1,3-propanediamine (0.22 mol) and 2-propenenitrile (0.22 mol) in ethanol (250 ml) was stirred overnight at room temperature. The solvent was evaporated. A mixture of 2,2-dimethyl-1,3-propanediamine (0.28 mol) and 2-propenenitrile (0.28 mol) in ethanol (250 ml) was stirred for one hour at room temperature. The solvent was evaporated. The residues were combined. This fraction was purified by distillation, yielding 27.2 g of 3-[(3-amino-2,2-dimethylpropyl)amino]-propanenitrile (intermediate 11).

b) A mixture of intermediate (11) (0.16 mol) and 1,1'-carbonylbis-1H-imidazole (0.16 mol) in THF (500 ml) was stirred and refluxed overnight. The precipitate was filtered off and dried, yielding 26.7 g of hexahydro-5,5-dimethyl-2-oxo-1-pyrimidinepropanenitrile (intermediate 12, mp. 190° C.).

c) A mixture of intermediate (12) (0.12 mol) in CH$_3$OH/NH$_3$ (400 ml) was hydrogenated with Raney Nickel (3.0 g) as a catalyst. After uptake of hydrogen (2 equivalents), the catalyst was filtered off and the filtrate was evaporated, yielding 21.2 g of 1-(3-aminopropyl)tetrahydro-5,5-dimethyl-2(1H)-pyrimidinone (intermediate 13).

EXAMPLE A.6 a) A mixture of 4-amino-1-(phenylmethyl)-4-piperidinemethanol (0.0182 mol) and 2-propenenitrile (0.0304 mol) in ethanol (80 ml) was stirred and refluxed for two days. 2-Propenenitrile (2 ml) was added. The mixture was stirred and refluxed for 5 hours. 2-Propenenitrile (2 ml) was added again. The mixture was stirred and refluxed overnight. The solvent was evaporated. The residue was purified over silica gel on a glass filter (eluent: CH$_2$Cl$_2$/(CH$_3$OH/NH3) 95/5). The desired fractions were collected and the solvent was evaporated, yielding 3-[[4-(hydroxymethyl)-1-(phenylmethyl)-4-piperidinyl]amino]-propanenitrile (intermediate 14).

b) A mixture of intermediate (14) (0.0159 mol) in methanol saturated with NH$_3$ (150 ml) was hydrogenated at 14° C. with Raney nickel (1/2 spoon) as a catalyst. After uptake of hydrogen (2 equivalents), the catalyst was filtered off and the filtrate was evaporated, yielding 3.8 g of 4-[(3-aminopropyl)amino]-1-(phenylmethyl)-4-piperidinemethanol (intermediate 15).

c) 1,1'-Carbonylbis-1H-imidazole (0.0149 mol) was added to a mixture of intermediate (15) (0.0137 mol) in THF (40 ml). The mixture was stirred at room temperature overnight. The precipitate was filtered off, crystallized from ACN, filtered off, washed with ACN and DIPE and then dried, yielding 2.05 g of tetrahydro-1-[4-(hydroxy-methyl)-1-(phenylmethyl)-4-piperidinyl]-2(1H)-pyrimidinone (intermediate 16, mp. 210° C.).

d) A mixture of intermediate (16) (0.0059 mol) in methanol (100 ml) was hydrogenated with palladium on carbon (1 g) as a catalyst. After uptake of hydrogen (1 equivalent), the catalyst was filtered off, the filtrate was evaporated and crystallized from ACN, yielding 0.6 g of tetrahydro-1-[4-(hydroxymethyl)-4-piperidinyl]-2(1H)-pyrimidinone (intermediate 17, mp. 162° C.).

EXAMPLE A.7

A reaction solution of 1-(2-propenyl)-2,4-imidazolidinedione (0.036 mol) and 3-chloro-benzenecarboperoxoic acid (0.043 mol, 70.75%) in DCM (25 ml) was stirred for 2 hours at room temperature. An aqueous solution of bisulfite was added and the mixture was stirred for 10 minutes. Na$_2$CO$_3$ was added and this mixture was extracted with DCM. The separated organic layer was dried, filtered and the solvent evaporated, yielding 5 g of (±)-1-(oxiranylmethyl)-2,4-imidazolidinedione (intermediate 18).

EXAMPLE A.8 a) Reaction was carried out under nitrogen flow. A mixture of 2-chloro-3-pyridinol hydrochloride (1:1) (1.760 mol) in DMF (1000 ml) was added dropwise in 30 minutes to a mixture of NaH 60% (1.934 mol) in DMF (1200 ml) (temperature below 27° C.). The reaction mixture was stirred for 30 minutes. (Chloromethyl)-oxirane (3.530 mol) in DMF (1200 ml) was added dropwise over 30 minutes. The reaction mixture was stirred for 9 hours at 60° C. The mixture was cooled. Water was added dropwise on an ice bath. The mixture was extracted with DCM. The organic layer was dried, filtered and the solvent was evaporated. Petroleum ether was added to the residue, then decanted (3 times). This fraction was combined with analogously obtained fractions, then purified by HPLC over silica gel (eluent: hexane/ethyl acetate (50/50)). The desired fractions were collected and the solvent was evaporated, yielding 635 g of 2-chloro-3-(oxiranylmethoxy)-pyridine (intermediate 19).

b) A mixture of THF (915 ml), benzenemethanol (2.96 mol) and NaOH (2.36 mol) was stirred at room temperature for 30 minutes (cooling was required to keep the temperature below 25° C.). Intermediate (19) (1.97 mol) was added. The reaction mixture was stirred at room temperature for 4 days. Water was added dropwise (cooling required) and the mixture was extracted with ethyl acetate. The organic layer was dried, filtered and the solvent was evaporated. The residue was combined with analogously obtained fraction, then purified by HPLC over silica gel (eluent: hexane/ethyl acetate (60/40)). The desired fractions were collected and the solvent was evaporated, yielding 38% of 1-[(2-chloro-3-pyridinyl)oxy]-3-[(3Z)-3,5-hexadienyloxy]-2-propanol (intermediate 20).

c) A mixture of intermediate (20) (0.034 mol) and Lawesson's Reagent (0.051 mol) in toluene (750 ml) was stirred and refluxed for 16 hours. The solvent was evaporated and the residue was purified by short open column chromatography over silica gel (eluent: CH$_2$Cl$_2$/2-propanone (100/0; 90/10)). The desired fractions were collected and the solvent was evaporated. The residue was purified by flash column chromatography over silica gel (eluent: hexane/2-propanone (95/5; 90/10)). The desired fractions were collected and the solvent was evaporated, yielding 2.3 g of 2,3-dihydro-3-[(phenylmethoxy)methyl]-[1,4]oxathiino[3,2-b]pyridine (intermediate 21).

d) A mixture of intermediate (21) (0.00732 mol) and FeCl$_3$ (2.37 g) in DCM (100 ml) was stirrred at room temperature for 16 hours. FeCl$_3$ (2.37 g) was added and the mixture was stirred for 16 hours more. The reaction mixture was basified with NH$_4$OH (saturated) and filtered through Celite. The organic layer was dried, filtered, and the solvent was evaporated. The residue was purified by short column chromatography over silica gel (eluent: CH$_2$Cl$_2$/2-propanone (95/5)). The desired fractions were collected and the solvent was evaporated, yielding 0.93 g of 2,3-dihydro-[1,4]oxathiino[3,2-b]pyridine-3-methanol (intermediate 22).

e) Methanesulfonyl chloride (0.0076 mol) was added slowly to a mixture of intermediate (22) (0.0051 mol) and triethylamine (0.0102 mol) in DCM (50 ml) at 0° C. The mixture was stirred at 0° C. for 2 hours. Water was added. The organic layer was dried, filtered, and the solvent was evaporated, yielding 1.16 g of 2,3-dihydro-[1,4]oxathiino[3,2-b]pyridine-3-methanol, methanesulfonate (ester) (intermediate 23).

EXAMPLE A.9 a) A mixture of NaH 60% (0.051 mol) in THF (20 ml) was stirred at 0° C. A solution of 3-hydroxy-2-pyridinecarboxaldehyde (0.034 mol) in THF (75 ml) was added dropwise at 0° C. The reaction mixture was stirred for one hour at room temperature. A solution of 2-(diethoxyphosphinyl)-2-propenoic acid, ethyl ester (0.041 mol) in THF (75 ml) was added portionwise at 0° C. The reaction mixture was stirred for 24 hours at room temperature, then stirred and refluxed for 4 hours, then stirred for 24 hours at room temperature. A 10% aqueous NHCl solution was added and the mixture was extracted with DCM. The separated organic layer was dried, filtered and the solvent evaporated. The residue was purified by short open column chromatography over silica gel. The desired fractions were collected and the solvent was evaporated, yielding 0.56 g of 2H-pyrano[3,2-b]pyridine-3-carboxylic acid, ethyl ester (intermediate 24).

b) A solution of intermediate (24) (0.0032 mol) in methanol (dry) (2 ml) and THF (dry) (16 ml) was stirred at 0° C. NaBH$_4$ (0.0128 mol) was added portionwise at 0° C. The reaction mixture was stirred for 5 hours at room temperature. A 10% NH$_4$Cl solution was added and this mixture was extracted with DCM. The separated organic layer was dried, filtered and the solvent evaporated, yielding 0.45 g of 2H-pyrano[3,2-b]pyridine-3-methanol (intermediate 25).

c) A mixture of intermediate (25) (0.0027 mol) in methanol (20 ml) was hydrogenated for 24 hours at room temperature with palladium-on-carbon (0.04 g) as a catalyst. After uptake of hydrogen (1 equivalent), the catalyst was filtered off and the filtrate was evaporated, yielding 0.35 g of 3,4-dihydro-2H-pyrano[3,2-b]pyridine-3-methanol (intermediate 26).

d) A solution of intermediate (26) (0.002 mol) in DCM (10 ml) was stirred at 0° C. Triethylamine (0.0024 mol) and methanesulfonyl chloride (0.0024 mol) were added at 0° C. and the resulting reaction mixture was stirred for 3 hours at room temperature. A saturated aqueous NaHCO$_3$ solution was added. The organic layer was separated, dried, filtered and the solvent was evaporated, yielding 0.49 g of 3,4-dihydro-2H-pyrano[3,2-b]pyridine-3-methanol, methanesulfonate (ester) (intermediate 27).

EXAMPLE A.10 a) To a solution of 2-chloro-3-pyridinamine (0.0465 mol) in THF (45 ml) at −78° C. under N$_2$ flow, lithium diisopropylamine (0.0513 mol, 2 M) was added dropwise. The mixture was allowed to warm to 0° C. and was stirred for 1 hour and then cooled to −78° C. Then iodomethane (0.0582 mol) was added and the reaction mixture was allowed to warm to room temperature and was stirred for 16 hours. A saturated NH$_4$Cl-solution was added and the mixture was extracted with ethyl acetate. The separated organic layer was dried, filtered and the solvent was evaporated. The residue was purified by short open column chromatography over silica gel (eluent: hexane/ethyl acetate 80/20). The product fractions were collected and the solvent was evaporated, yielding 5.91 g of 2-chloro-N-methyl-3-pyridinamine (intermediate 28).

b) To a solution of intermediate (28) (0.031 mol) in THF (50 ml) under nitrogen flow at −78° C., lithium diisopropylamine (0.062 mol, 2 M) was slowly added. The reaction mixture was allowed to warm to 0° C. and was stirred for 1 hour. After cooling again to −78° C., a solution of [(phenylmethoxy)methyl]-oxirane (0.034 mol) in THF (40 ml) was added and the mixture was allowed to warm to room temperature and was stirred for 16 hours. A saturated NH$_4$Cl-solution was added and the mixture was extracted with ethyl acetate. The separated organic layer was dried, filtered and the solvent was evaporated. The residue was purified by short open column chromatography over silica gel (eluent: hexane/ethyl acetate 50/50). The product fractions were collected and the solvent was evaporated, yielding 7.18 g of 1-[(2-chloro-3-pyridinyl)methylamino]-3-(phenylmethoxy)-2-propanol (intermediate 29).

c) To a suspension of NaH 60% (0.081 mol) in DME (250 ml), a solution of intermediate (29) (0.023 mol) in DME (250 ml) was added dropwise. The reaction mixture was stirred and refluxed for 16 hours. After cooling, the mixture was taken up in H$_2$O/ethyl acetate. The separated organic layer was dried, filtered and the solvent was evaporated. The residue was purified by short open column chromatography over silica gel (eluent: hexane/ethyl acetate 95/5). The desired fractions were collected and the solvent was evaporated, yielding 5.82 g of 1-[(2-chloro-3-pyridinyl)methylamino]-3-(phenylmethoxy)-2-propanol (intermediate 30).

d) A mixture of intermediate (30) (0.018 mol) and FeCl$_3$ (0.036 mol) in DCM (500 ml) was stirred at room temperature for 16 hours. Then FeCl$_3$ (0.018 mol) was added and the mixture was stirred for 6 hours more. Extra FeCl$_3$ (0.018 mol) was added again and the mixture was stirred for 16 hours. The reaction mixture was basified with a saturated NH$_4$Cl-solution and the formed precipitate was filtered over dicalite. The separated organic layer was extracted with a saturated NH$_4$Cl-solution, dried, filtered and the solvent was evaporated. The residue was purified by short open column chromatography over silica gel (eluent: CH$_2$Cl$_2$/(MeOH/NH$_3$) 95/5). The product fractions were collected and the solvent was evaporated. The residue was purified again by short open column chromatography over silica gel (eluent: ethyl acetate/(MeOH/NH$_3$) 98/2; 95/5). The desired fractions were collected and the solvent was evaporated, yielding 2.1 g of 2,3-dihydro-1-methyl-1H-pyrido[2,3-b][1,4]oxazine-3-methanol (intermediate 31).

e) To a solution of intermediate (31) (0.0111 mol) and thriethylamine (0.0222 mol) in DCM (200 ml) at 0° C., methanesulfonyl chloride (0.0166 mol) was added dropwise.

The reaction mixture was stirred at 0° C. for 1 hour. Then water was added. The separated organic layer was extracted with brine, dried, filtered and the solvent was evaporated, yielding 2.85 g of 2,3-dihydro-1-methyl-1H-pyrido[2,3-b][1,4]oxazine-3-methanol, methanesulfonate (ester) (intermediate 32).

EXAMPLE A.11 a) A solution of 3-chloro-benzenecarboperoxoic acid (0.087 mol) in trichloromethane (125 ml) was added dropwise to a solution of 2,3-dihydro-1,4-dioxino[2,3-b]pyridine-3-methanol methanesulfonate ester (0.0217 mol) in trichloromethane (125 ml) and it was stirred at room temperature overnight. 50 ml of methanol and 12.47 g of $K_2CO_3$ were added and the mixture was stirred for 30 minutes. Then, it was filtered off and the solid was washed with a mixture of DCM in methanol (90/10). The filtrate was evaporated till dryness and the residue was purified by open column chromatography over silica gel (eluent: $CH_2Cl_2$/(MeOH/$NH_3$) 96/4, 95/5 and 90/10). The product fractions were collected and the solvent was evaporated, yielding 3.62 g of 2,3-dihydro-[1,4]dioxino[2,3-b]pyridine-3-methanol, methanesulfonate (ester) (intermediate 33).

b) A mixture of intermediate (33) (0.0138 mol) and phosphorus oxychloride (0.069 mol) was stirred for 3 hours at 100° C. The crude reaction mixture was evaporated till dryness. The cooled residue was carefully treated with water and then it was neutralized with $Na_2CO_3$. The mixture was extracted with DCM. The separated organic layer was dried, filtered and evaporated till dryness, yielding 3.17 g of 6-chloro-2,3-dihydro-[1,4]dioxino[2,3-b]pyridine-3-methanol, methanesulfonate (ester) (intermediate 34).

EXAMPLE A.12 a) Bromine (0.009 mol) was added dropwise to a solution of 2,3-dihydro-1,4-dioxino[2,3-b]pyridine-3-methanol (0.009 mol) in DCM (100 ml) and $Na_2CO_3$ saturated solution (50 ml), stirred at room temperature. The reaction mixture was stirred for 16 hours at room temperature. More bromine (0.009 mol) was added and the reaction mixture was stirred for 3 more days at room temperature. A few drops of $Na_2SO_3$ were added and the mixture was stirred for 15 minutes. The separated organic layer was dried, filtered and the solvent evaporated. The residue was purified by short open column chromatography over silica gel (eluent: $CH_2Cl_2$/$CH_3OH$ 100/0; 98/2). The desired fractions were collected and the solvent was evaporated, yielding 0.9 g of 7-bromo-2,3-dihydro-[1,4]dioxino[2,3-b]pyridine-3-methanol (intermediate 35).

b) Methanesulfonyl chloride (0.0054 mol) was added dropwise to a mixture of intermediate (35) (0.0036 mol) and triethylamine (0.0072 mol) in DCM (50 ml), stirred at 0° C. The reaction mixture was stirred for 30 minutes at 0° C., and then it was extracted with water. The organic layer was separated, dried, filtered and the solvent was evaporated, yielding 1.07 g of 7-bromo-2,3-dihydro-[1,4]dioxino[2,3-b]pyridine-3-methanol, methanesulfonate (ester) (intermediate 36).

EXAMPLE A.13 a) Chloro(1,1-dimethylethyl)dimethyl-silane (0.020 mol) was added dropwise to a solution of intermediate (38) (0.010 mol) and 1H-imidazole (0.020 mol) in DMF (100 ml) and the reaction mixture was stirred for 16 hours at room temperature. The solvent was evaporated. The residue was taken up into water/ethyl acetate. The organic layer was separated, dried, filtered and the solvent was evaporated. The residue was purified by short open column chromatography over silica gel (eluent: hexane/ethyl acetate 90/100. The desired fractions were collected and the solvent was evaporated, yielding 2.4 g of 7-bromo-3-[[[(1,1-dimethylethyl)dimethylsilyl]oxy]methyl]-2,3-dihydro-[1,4]dioxino[2,3-b]pyridine (intermediate 37).

b) Reaction under nitrogen atmosphere. A solution of intermediate (37) (0.00194 mol) in THF was cooled to −78° C. BuLi (0.00214 mol, 2.5M) was added dropwise and the mixture was stirred for 75 minutes at −78° C. Then, iodomethane (00214 mol) was added and the reaction mixture was stirred for 45 minutes. A saturated aqueous $NH_4Cl$ solution was added and the mixture was allowed to warm to room temperature. This mixture was extracted with ethyl acetate. The separated organic layer was dried, filtered and the solvent evaporated. The residue was purified by flash column chromatography over silica gel (eluent: hexane/ethyl acetate 80/20). The desired fractions were collected and the solvent was evaporated, yielding 0.24 g of 3-[[[(1,1-dimethylethyl)dimethyl-silyl]oxy]methyl]-2,3-dihydro-7-methyl-[1,4]dioxino[2,3-b]pyridine (intermediate 38).

c) Reaction under nitrogen atmosphere. TBAF, 1M/THF (0.00122 mol) was added to a solution of intermediate (41) (0.00081 mol) in THF anhydrous (5 ml), stirred at room temperature. The reaction mixture was stirred for 16 hours. Water was added. This mixture was extracted with ethyl acetate. The separated organic layer was dried, filtered and the solvent evaporated, yielding 0.147 g of 2,3-dihydro-7-methyl-[1,4]dioxino-[2,3-b]pyridine-3-methanol (intermediate 39).

d) Methanesulfonyl chloride (0.00103 mol) was added to a mixture of intermediate (39) (0.00081 mol) and triethylamine (0.0019 mol) in DCM, stirred at 0° C. The reaction mixture was stirred for 30 minutes at 0° C. Water was added. The organic layer was separated, dried, filtered and the solvent was evaporated, yielding 0.208 g of 2,3-dihydro-7-methyl-[1,4]dioxino[2,3-b]pyridine-3-methanol methanesulfonate (ester) (intermediate 40).

EXAMPLE A.14 a) To a solution of intermediate (2-a) (0.03 mol) in DCM (50 ml) and $Na_2CO_3$ saturated (50 ml), bromine (0.09 mol) was added dropwise and the reaction mixture was stirred for 16 hours at room temperature. Then a $Na_2SO_3$-solution (10%) was added and the mixture was stirred for 5 minutes at room temperature and then neutralized with a saturated $Na_2CO_3$-solution. The aqueous layer was extracted with DCM and the separated combined organic layers were dried, filtered and the solvent was evaporated. The residue was purified by short open column chromatography over silica gel (eluent: $CH_2Cl_2$/(MeOH/$NH_3$ saturated) 95/5). The desired fractions were collected and the solvent was evaporated. The residue was purified by high-performance liquid chromatography over silica gel (eluent: $CH_2Cl_2$/(MeOH/$NH_3$ saturated) 97/3). The product fractions were collected and the solvent was evaporated, yielding 2.7 g of (S)-7-bromo-2,3-dihydro-[1,4]dioxino[2,3-b]pyridine-3-methanol (intermediate 41) and 0.26 g of 8-bromo-2,3-dihydro-[1,4]dioxino[2,3-b]pyridine-3-methanol (intermediate 42)

b) To a mixture of intermediate (42) (0.0014 mol) and triethylamine (0.0028 mol) in DCM (5 ml), methanesulfonyl chloride (0.0021 mol) was slowly added at room temperature. The reaction mixture was stirred for 16 hours and was then extracted with water. The separated organic layer was dried, filtered and the solvent was evaporated, yielding 0.42 g of (S)-8-bromo-2,3-dihydro-[1,4]dioxino[2,3-b]pyridine-3-methanol methanesulfonate (ester) (intermediate (43).

EXAMPLE A.15 a) A solution of diazenedicarboxylic acid diethyl ester (0.1572 mol) in THF (163 ml) was added dropwise to a mixture of 4-chloro-3-pyridinol (0.1429 mol), 2-propen-1-ol (0.1572 mol) and triphenyl-phosphine (0.1572 mol) in THF (276 ml), that was cooled with an ice-water bath and under nitrogen flow. The formed mixture was stirred on the ice-water bath for 15 minutes and at room temperature overnight. The mixture was concentrated under vacuum and the residue was washed with a saturated $Na_2CO_3$-solution. The mixture was extracted with DCM and the separated organic layer was dried, filtered and the solvent was evaporated until dry. The residue was treated with DIPE and the formed solid was filtered off and discarded. The filtrate was evaporated until dry and the residue was treated with diethyl ether and the formed solid was filtered off and discarded again. The filtrate was evaporated until dry and the residue was purified by open column chromatography over silica gel (eluent: DCM/2-propanone 99/1; 98/2). The product fractions were collected and the solvent was evaporated, yielding 7.9 g of 4-chloro-3-(2-propenyloxy)-pyridine (intermediate (44).
b) To a mixture of NaH 60% (0.11 mol) in DME (170 ml), under nitrogen flow, benzenemethanol (0.0698 mol) was added dropwise and the mixture was stirred at room temperature for 30 minutes. Then a solution of intermediate (44) (0.046 mol) in DME (170 ml) was added dropwise and the resulting mixture was stirred and refluxed overnight. The cooled reaction mixture was washed with water and extracted with ethyl acetate. The separated organic layer was dried, filtered and the solvent was evaporated until dry. The residue was purified by open column chromatography over silica gel (eluent: DCM/2-propanone/MeOH 100/0/0; 96/4/0; 96/0/4; 90/0/10). The product fractions were collected and the solvent was evaporated, yielding 6.2 g of 4-(phenylmethoxy)-3-(2-propenyloxy)-pyridine (intermediate 45).
c) To a solution of intermediate (45) (0.0256 mol) in DCM (64 ml), bromine (0.0256 mol) was added dropwise and the mixture was stirred at room temperature for 30 minutes. The reaction mixture was washed with a saturated $NaHCO_3$-solution and a few drops of $Na_2SO_3$-solution 10% and it was extracted. The separated organic layer was dried, filtered and the solvent was evaporated until dry. The residue was purified by open column chromatography (eluent: DCM/MeOH 100/0,99/1,98/2). The product fractions were collected and the solvent was evaporated, yielding 6.68 g of 3-(2,3-dibromopropoxy)-4-(phenylmethoxy)-pyridine (intermediate 46).
d) To a solution of intermediate (46) (0.0166 mol) in DCM (270 ml), $FeCl_3$ (0.033 mol) was added portionwise and the mixture was stirred at room temperature overnight. The reaction mixture was treated with a saturated $NH_4Cl$-solution and with a diluted solution of potassium sodium tartrate and then it was filtered off over celite. The solvent was evaporated until dry and the residue was treated with methanol and then filtered off. The filtrate was evaporated until dry and the residue was treated with 2,3-dihydroxy butaenedioic acid, monopotassium monosodium salt (1 g)

in ethanol and refluxed for 18 hours. The cooled reaction mixture was filtered off over celite and the filtrate was evaporated until dry. The residue was washed with water and extracted with DCM. The separated organic layer was dried, filtered and the solvent was evaporated until dry. The residue was purified by flash column chromatography over silica gel (eluent: ethyl acetate/(MeOH/$NH_3$) 96/4). The product fractions were collected and the solvent was evaporated, yielding 0.52 g of 2-(bromomethyl)-2,3-dihydro-[1,4]dioxino-[2,3-c]pyridine (intermediate 47).

EXAMPLE A.16 a) 5-Bromo-pyrimidine (0.063 mol) was slowly added to 2-propen-1-ol (4.03 mol) at 0° C. and this mixture was stirred at room temperature for 1 hour. Then NaH 60% (0.126 mol) was added and the reaction mixture was stirred and refluxed for 48 hours. Water was added and the mixture was extracted with ethyl acetate. The separated organic layer was dried, filtered and the solvent was evaporated. The residue was purified by short open column chromatography over silica gel (eluent: hexane/ethyl acetate 50/50). The desired fractions were collected and the solvent was evaporated, yielding 2.3 g of 5-(2-propenyloxy)-pyrimidine (intermediate 48).
b) To a solution of intermediate (48) (0.0169 mol) in DCM (250 ml), bromine (0.0186 mol) was slowly added and the reaction mixture was stirred at room temperature for 1 hour. The solvent was extracted with a saturated $Na_2CO_3$-solution and a few drops of a $Na_2SO_3$-solution (10%). The separated organic layer was dried, filtered and the solvent was evaporated. The residue was purified by short open column chromatography over silica gel (eluent: hexane/ethyl acetate 66/33; 50/50). The desired fractions were collected and the solvent was evaporated, yielding 3.85 g of 3-(2,3-dibromopropoxy)-pyridine (intermediate 49).
c) To a solution of intermediate (49) (0.0123 mol) and $H_2SO_4$ (0.0135 mol) in water (5 ml), $CH_3CO_3H$ 35% (0.0246 mol) was added dropwise and the reaction mixture was stirred at room temperature for 16 hours. The mixture was extracted with ethyl acetate. The separated organic layer was dried, filtered and the solvent was evaporated. The residue was purified by short open column chromatography over silica gel (eluent: ethyl acetate/(MeOH/$NH_3$) 95/5). The desired fractions were collected and the solvent was evaporated, yielding 2.83 g of 5-(2,3-dibromopropoxy)-4(3H)-pyrimidinone (intermediate 50).
d) A mixture of intermediate (50) (0.0091 mol) and $NaHCO_3$ (0.0113 mol) in ethanol (100 ml) was stirred and refluxed for 16 hours. The reaction mixture was allowed to cool to room temperature and the solvent was evaporated. The residue was taken up in water and ethyl acetate. The separated organic layer was dried, filtered and the solvent was evaporated. The residue was purified by short open column chromatography over silica gel (eluent: hexane/ethyl acetate 66/33; 50/50). The desired fractions were collected and the solvent was evaporated, yielding 1.1 g of 7-(bromomethyl)-6,7-dihydro-[1,4]dioxino[2,3-d]pyrimidine (intermediate 51).

EXAMPLE A.17 a) Reaction under an argon flow. A mixture of 1-amino-3-dibenzylaminopropane (0.195 mol) in ethanol (225 ml) was stirred at room temperature. Ethyl propenoate (0.2 mol) was poured into the mixture and the reaction mixture was stirred overnight at room temperature. The solvent was evaporated. The residue was purified by column chromatography over silica gel (eluent: CH$_2$Cl$_2$/hexane/CH$_3$OH 50/45/5). The desired fractions were collected and the solvent was evaporated, yielding 27 g of N-[3-[bis(phenylmethyl)amino]propyl]-β-alanine, ethyl ester (intermediate 52).

b) Intermediate (52) was stirred in ethanol (150 ml). The mixture was acidified with HCl/2-propanol (±60 ml)+water (2 ml). The mixture was stirred for 15 minutes. The solvent was evaporated at 60° C. Ethanol was added to the residue. The solvent was evaporated. A mixture of methanol in water (70:30; 200 ml) was added to the residue and the mixture was stirred, then warmed slightly until complete dissolution. The acidic solution was added dropwise (over 30 minutes, under argon) to a solution of KOCN (0.100 mol) in a mixture of methanol in water (70:30; 100 ml), stirred at room temperature pH went from ±8 to ±6). The reaction mixture was stirred for 19 hours at room temperature. More KOCN (0.32 g) was added and the reaction mixture was stirred for 90 minutes at room temperature. More KOCN (0.9 g) was added and the reaction mixture was stirred for 75 minutes at room temperature, then for 6 days at 95° C. The reaction mixture was cooled. Concentrated HCl (20 ml) was added dropwise. The reaction mixture was stirred for 2 hours at 95° C., then stood overnight at room temperature. The precipitate was filtered off, and the filtrate was stirred and cooled for 3 hours on an ice-bath. The resulting precipitate was filtered off and dried, yielding 19.6 g of 1-[3-[bis(phenylmethyl)amino]propyl]dihydro-2,4(1H,3H)-pyrimidinedione (intermediate 53).

c) A mixture of intermediate (53) (0.010 mol) in methanol (150 ml) was hydrogenated at 50° C. with palladium-on-carbon (10%, 1 g) as a catalyst. After uptake of hydrogen (2 equivalents), the catalyst was filtered off and the filtrate was evaporated. Toluene was added and azeotroped on the rotary evaporator. The residue was dried over the weekend under a gentle stream of nitrogen. Toluene was added and azeotroped on the rotary evaporator. The residue was stirred in DCM (50 ml). NaOCH3 (0.504 g) was added and the reaction mixture was stirred for one hour under nitrogen. More methanol (25 ml) was added and the mixture was stirred for 30 minutes. The precipitate was filtered off and the filtrate was evaporated in vacuo, yielding 1.54 g of 1-(3-aminopropyl)dihydro-2,4(1H,3H)-pyrimidinedione (intermediate 54).

B. Preparation of the Final Compounds

EXAMPLE B.1

A mixture of intermediate (1) (0.00815 mol), 1-(3-aminopropyl)tetrahydro-2(1H)-pyrimidinone (0.00815 mol) and CaO (0.022 mol) in (26.5 ml) was stirred at 100° C. overnight in a Parr apparatus. The excess of CaO was filtered off. The filtrate was evaporated till dryness. The residue was purified by open column chromatography over silica gel (eluent 1: CH$_2$Cl$_2$/CH$_3$OH 90/10 and eluent 2: CH$_2$Cl$_2$/(CH$_3$OH/NH$_3$) 96/4). The pure fractions were collected and the solvent was evaporated. The residue was purified again by HPLC over silica gel (eluent: CH$_2$Cl$_2$/(CH$_3$OH/NH$_3$) 93/7). The pure fractions were collected and the solvent was evaporated. The residue was crystallized from DIPE. The precipitate was filtered off and dried, yielding 0.88 g of (±)-1-[3-[[(2,3-dihydro-1,4-dioxino[2,3-b]pyridin-3-yl)methyl]amino]propyl]tetrahydro-2(1H)pyrimidinone (compound 1).

EXAMPLE B.2

A mixture of intermediate (6) (0.0092 mol) and intermediate (13) (0.0183 mol) was stirred for 2 hours at 100° C. The crude reaction mixture was purified by open column chromatography over silica gel (eluent: CH$_2$Cl$_2$/CH$_3$OH 90/10). The desired fractions were collected and the solvent was evaporated. The residue was washed with DIPE, then dried, yielding 1.48 g of (±)-1-[3-[(1,3-dioxolo[4,5-b]pyridin-2-ylmethyl)amino]-propyl]tetrahydro-5,5-dimethyl-2(1H)-pyrimidinone (compound 10).

EXAMPLE B.3

A mixture of 2-(bromomethyl)-3,4-dihydro-2H-pyrano[2,3-b]pyridine (0.007 mol) and 1-(3-aminopropyl)tetrahydro-2(1H)-pyrimidinone (0.014 mol) was stirred for 2 hours at 100° C. The crude reaction mixture was treated with DCM and the resulting solid was filtered off and discarded. The filtrate was evaporated and the residue was purified by open column chromatography over silica gel (eluent: CH$_2$Cl$_2$/CH$_3$OH 84/16, CH$_2$Cl$_2$/(CH$_3$OH/NH$_3$) 90/10). The purest fractions were collected and the solvent was evaporated. The residue was dissolved in ethanol and converted into the ethanedioic acid salt (1:1), then filtered off and recrystallized from ethanol, yielding 0.45 g of (±)-1-[3-[[(3,4-dihydro-2H-pyrano[2,3-b]pyridin-2-yl)methyl]amino]propyl]tetrahydro-2(1H)-pyrimidinone ethanedioate (1:1) (compound 9).

EXAMPLE B.4

A mixture of 2,3-dihydro-N-(phenylmethyl)-1,4-dioxino[2,3-b]pyridine-3-methanamine (0.0059 mol) and intermediate (18) (0.00497 mol) in methanol (30 ml) was stirred and refluxed overnight. The solvent was evaporated. The residue was purified by short open column chromatography over silica gel (eluent: CH$_2$Cl$_2$/2-propanone 96/4, 90/10 and 80/20), then CH$_2$Cl$_2$/CH$_3$OH 96/4 and 90/10). The product fractions were collected and the solvent was evaporated, yielding 1.29 g of (±)-1-[3-[[(2,3-dihydro-1,4-dioxino-[2,3-b]pyridin-3-yl)methyl](phenylmethyl)amino]-2-hydroxypropyl]-2,4-imidazolidine-dione (compound 12).

EXAMPLE B.5

A solution of compound (12) (0.0031 mol) in methanol (40 ml) was hydrogenated in Parr apparatus at 50° C. with palladium-on-carbon (10%, 0.13 g) as a catalyst. After uptake of hydrogen (1 equivalent), the catalyst was filtered off and the filtrate was evaporated. The residue was purified by HPLC over silica gel (eluent: CH$_2$Cl$_2$/(CH$_3$OH/NH$_3$) gradient from 90/10 to 92.5/7.5). The product fractions were collected and the solvent was evaporated, yielding 0.3 g of 1-[3-[[(2,3-dihydro-1,4-dioxino[2,3-b]pyridin-3-yl)methyl]amino]-2-hydroxypropyl]-2,4-imidiazolidinedione (compound 13).

EXAMPLE B.6

Potassium hydroxide (0.0022 mol) in ethanol was added to compound (44) (0.0012 mol) in ethanol. The reaction mixture was stirred for 4 hours at 50° C., then overnight at room temperature. The solvent was evaporated. The residue was purified by HPLC over RP BDS (Hyperprep C18 (100 Å, 8 μm; eluent: H$_2$O/CH$_3$CN (0 min) 100/0, (24 min) 63/37, (24.01-32 min) 0/100). The product fractions were collected and the solvent was evaporated, yielding 0.050 g of compound (50).

EXAMPLE B.7

Reaction under nitrogen atmosphere. Compound (R268652) (0.0037 mol) was stirred in THF (120 ml), and cooled on an ice-water bath. Lithiumborohydride (0.0074 mol; 3.7 ml of a 2 M solution in THF) was added and the reaction mixture was stirred for one hour at room temperature. The mixture was stirred and refluxed for 5 hours, then stirred over the weekend at room temperature, then stirred and refluxed overnight, and finally cooled to room temperature. More lithiumborohydride (0.0074 mol) was added and the reaction mixture was stirred and refluxed overnight, then cooled to room temperature. Water was added. The mixture was alkalized with 50% NaOH, and then the organic solvent (THF) was evaporated. The residue was purified by column chromatography over silica gel (eluent: $CH_2Cl_2/CH_3OH$ 95/5). The desired fractions were collected and the solvent was evaporated. The residue was taken up into a small amount of ACN, warmed until complete dissolution, then cooled on an ice-bath and the resulting precipitate was filtered off, washed and dried, yielding 0.7 g of compound (51).

EXAMPLE B.8

A solution of meta-chloroperbenzoic acid (0.0027 mol) in chloroform (34 ml) was added dropwise to a solution of compound (14) (0.0024 mol) in chloroform (8 ml) that was cooled to −50° C. The mixture was stirred for 1 hour at a temperature −50° C. to −20° C. Then methanol and $K_2CO_3$ were added. The formed mixture was stirred at room temperature for 30 minutes and then it was filtered off. The solid was washed with $CH_2Cl_2/CH_3OH$(80/20) and the filtrate was evaporated till dryness. The mixture was purified by flash column chromatography with $CH_2Cl_2/CH_3OH/(CH_3OH/NH_3)$ (80/20/0; 85/0/15; 80/0/20). The product fractions were collected and washed with DCM. The solvent was filtered and evaporated, yielding 0.44 g of compound (40).

EXAMPLE B.9

Compound (60) (0.0091 mol) was purified and separated by high performance liquid chromatography over Chiralpak AD (eluent: $C_2H_5OH/CH_3CN$ (64/36)). The product fractions were collected, the solvent was evaporated, and each residue was dissolved in ethanol and converted into the ethanedioic acid salt (1:1). Yielding 0.7 g of compound (27), $[\alpha]_D^{20}$=−42.50° (c=25.06 mg/5 ml in $CH_3OH$), mp. 212° C.; and 0.9 g of compound (28), $[\alpha]_D^{20}$=+42.77° (c=25.72 mg/5 ml in $CH_3OH$), mp. 216° C.

EXAMPLE B.10

A mixture of intermediate (3) (0.04 mol), 1-(4-piperidinyl)-2-imidazolidinone (0.05 mol) and $NaHCO_3$ (0.09 mol) in 1,4-dioxane (300 ml) was stirred and refluxed for 60 hours. The solvent was evaporated. The residue was partitioned between water and DCM. The separated organic layer was dried, filtered and the solvent evaporated. The residue was purified by column chromatography over silica gel (eluent: $CH_2Cl_2/CH_3OH$ 95/5). The desired fractions were collected and the solvent was evaporated. The residue was solidified in DIPE, filtered off and dried, yielding 6.13 g (48.3%) of compound (19) (mp. 132° C.; $[\alpha]_D^{20}$ =−41.70° (c=24.34 mg/5 ml in methanol.

EXAMPLE B.11

A mixture of intermediate (54) (0.058 mol) in dioxane (400 ml) was stirred. A mixture of intermediate (3) (0.029 mol) and CaO (2.4 g) was added. The reaction mixture was stirred at 140° C. for 16 hours. The solvent was evaporated. DCM and water was added to the residue. The separated organic layer was dried, filtered and the solvent was evaporated. The residue was purified by high-performance liquid chromatography over silica gel (eluent: $CH_2Cl_2/(CH_3OH/NH_3)$ 90/10). The product fractions were collected and the solvent was evaporated. The residue was dissolved in ethanol and converted into the ethanedioic acid salt (1:1). The formed precipitate was filtered off and dried, yielding 1.5 g of (S)-1-[3-[[(2,3-dihydro[1,4]dioxino[2,3-b]pyridin-3-yl)methyl]amino]-propyl]dihydro-2,4(1H,3H)-pyrimidinedione (compound 25), mp. 186; $[\alpha]_D^{20}$=−37.46°(c=26.56 mg/5 ml DMF).

EXAMPLE B.12 a) A mixture of intermediate (3) (0.041 mol), benzylamine (0.041 mol) and $NaHCO_3$ (0.11 mol) in dioxane (100 ml) was stirred and refluxed for 48 hours. The solvent was evaporated. The residue was taken up in water and DCM. The separated organic layer was dried, filtered and the solvent was evaporated. The residue was purified by column chromatography over silica gel (eluent: $CH_2Cl_2/CH_3OH$ 95/5). The desired fractions were collected, the solvent was evaporated, yielding (S)-2,3-dihydro-N-(phenylmethyl)-[1,4]dioxino[2,3-b]pyridine-3-methanamine (intermediate 55).

b) Intermediate (55) (0.0195 mol) was dissolved in ethanol (50 ml). 2-Propenenitrile (0.02 mol) was added and the reaction mixture was stirred and refluxed overnight. Additional 2-propenenitrile (0.02 mol) was added and the reaction mixture was stirred and refluxed for 2 hours. Additional 2-propenenitrile (0.02 mol) was added and the reaction mixture was stirred and refluxed for 6 hours. Additional 2-propenenitrile (0.02 mol) was added and the reaction mixture was stirred and refluxed overnight. The solvent was evaporated. The residue was purified by column chromatography over silica gel (eluent: $CH_2Cl_2/CH_3OH$ 97/3). The product fractions were collected and the solvent was evaporated, yielding 6.0 g of (S)-3-[[(2,3-dihydro[1,4]dioxino[2,3-b]pyridin-3-yl)methyl](phenylmethyl)amino]-propanenitrile (intermediate 56).

c) A mixture of intermediate (56) (0.0195 mol) in methanol saturated with $NH_3$ (400 ml) was hydrogenated with Raney nickel (1 g) as a catalyst. After uptake of hydrogen (2 equivalents), the catalyst was filtered off and the filtrate was evaporated. The residue was purified by column chromatography over silica gel (eluent: $CH_2Cl_2/(CH_3OH/NH_3)$ 90/10). The product fractions were collected and the solvent was evaporated, yielding 2.7 g of (S)—$N^1$-[(2,3-dihydro[1,4]dioxino[2,3-b]pyridin-3-yl)methyl]-$N^1$-(phenylmethyl)-1,3-propanediamine (intermediate 57).

d) Ethyl monobromoacetate (0.0032 mol) was dissolved in THF (30 ml). This solution was added dropwise and slowly to a mixture of intermediate (57) (0.0032 mol) and triethylamine (0.0048 mol) in THF (50 ml). The reaction mixture was stirred overnight at room temperature. The solvent was evaporated. The residue was partitioned between water and DCM. The organic layer was separated, dried, filtered and the solvent was evaporated. The residue was purified by column chromatography over silica gel (eluent: $CH_2Cl_2/(CH_3OH/NH_3)$ 99/1). The desired fractions were collected and the solvent was evaporated, yielding 0.8 g of (S)-[[3-[[(2,3-dihydro[1,4]dioxino[2,3-b]pyridin-3-yl)methyl](phenylmethyl)amino]propyl]amino]-acetic acid, ethyl ester (intermediate 58).

e) A mixture of intermediate (59) (0.002 mol) in dioxane (7.3 ml) and THF (2.4 ml) was stirred at room temperature. Trimethylsilyl isocyanate (0.0023 mol) was added and the reaction mixture was stirred and refluxed for one hour. The solvent was evaporated. The residue was dissolved in HCl (6 N, 6.2 ml), then stirred and refluxed for one hour. The reaction mixture was cooled, poured out into NH$_4$OH/ice, and extracted with DCM. The separated organic layer was dried, filtered and the solvent evaporated, yielding 0.4 g of (S)-1-[3-[[(2,3-dihydro[1,4]dioxino[2,3-b]pyridin-3-yl)methyl]-(phenylmethyl)amino]propyl]-2,4-imidazolidinedione (intermediate 60).

f) A mixture of intermediate (61) (0.001 mol) in methanol (50 ml) was hydrogenated with palladium-on-carbon (0.2 g) as a catalyst. After uptake of hydrogen (1 equivalent), the catalyst was filtered off and the filtrate was evaporated. The residue was dissolved in ethanol and converted into the ethanedioic acid salt (1:1), yielding 0.3 g of compound (30), (mp. 190° C.; $[\alpha]_D^{20}$ = –35.99° (c=24.87 mg/5 ml in DMF).

Table F-1 to F-7 list the compounds that were prepared according to one of the above Examples. The following abbreviations were used: .C$_2$H$_2$O$_4$ stands for the ethanedioate salt

TABLE F-1

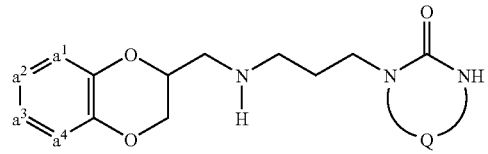

| Co No. | Ex. No. | —a$^1$=a$^2$—a$^3$=a$^4$— | —Q— | Physical data (mp. in ° C.) |
|---|---|---|---|---|
| 1 | B.1 | —N=CH—CH=CH— | —(CH$_2$)$_3$— | mp. 77.5 |
| 2 | B.1 | —N=CH—CH=CH— | —(CH$_2$)$_3$— | (A); .C$_2$H$_2$O$_4$ (1:1); $[\alpha]_D^{20}$ = +44.40° (c = 24.66 mg/5 ml in methanol) |
| 3 | B.1 | —N=CH—CH=CH— | —(CH$_2$)$_3$— | (B); .C$_2$H$_2$O$_4$ (1:1); mp. 203; $[\alpha]_D^{20}$ = –44.65° (c = 24.75 mg/5 ml in methanol) |
| 4 | B.1 | —N=CH—CH=CH— | —CH$_2$—C(CH$_3$)$_2$—CH$_2$— | .C$_2$H$_2$O$_4$ (1:1); mp. 164.9 |
| 5 | B.1 | —CH=CH—CH=N— | —CH$_2$—C(CH$_3$)$_2$—CH$_2$— | — |
| 6 | B.2 | —N=CH—CH=CH— | —CH$_2$—CO— | .C$_2$H$_2$O$_4$ (1:1) |
| 7 | B.2 | —N=CH—CH=CH— | —CH$_2$—CH$_2$—CO— | — |
| 8 | B.3 | —CH=N—CH=CH— | —(CH$_2$)$_3$— | .C$_2$H$_2$O$_4$ (1:1) |
| 25 | B.11 | —N=CH—CH=CH— | —CH$_2$—CH$_2$—CO— | (S); .C$_2$H$_2$O$_4$ (1:1); mp. 186; $[\alpha]_D^{20}$ = –37.46° (c = 26:56 mg/5 ml DMF) |
| 26 | B.2 | —N=CH—CBr=CH— | —(CH$_2$)$_3$— | .C$_2$H$_2$O$_4$ (1:1); |
| 27 | B.9 | —CH=N—CH=CH— | —(CH$_2$)$_3$— | (A); .C$_2$H$_2$O$_4$ (1:1); mp. 212° C.; $[\alpha]_D^{20}$ = –42.50° (c = 25.06 mg/5 ml in CH$_3$OH) |
| 28 | B.9 | —CH=N—CH=CH— | —(CH$_2$)$_3$— | (B); .C$_2$H$_2$O$_4$ (1:1); mp. 216° C.; $[\alpha]_D^{20}$ = +42.77° (c = 25.72 mg/5 ml in CH$_3$OH) |
| 29 | B.3 | —N=CH—N=CH— | —(CH$_2$)$_3$— | .C$_2$H$_2$O$_4$ (1:1); |
| 30 | B.12 | —N=CH—CH=CH— | —CH$_2$—CO— | (S); .C$_2$H$_2$O$_4$ (1:1); mp. 190; $[\alpha]_D^{20}$ = –35.99° (c = 24.87 mg/5 ml DMF) |
| 60 | B.3 | —CH=N—CH=CH— | —(CH$_2$)$_3$— | — |

TABLE F-2

| Co No. | Ex. No. | —a¹=a²—a³=a⁴— | —Q— | Physical data (mp. in °C.) |
|---|---|---|---|---|
| 9 | B.2 | —N=CH—CH=CH— | —(CH$_2$)$_3$— | .C$_2$H$_2$O$_4$ (1:1); mp. 195.7 |

TABLE F-3

| Co No. | Ex. No. | —a¹=a²—a³=a⁴— | —Q— | Physical data (mp. in °C.) |
|---|---|---|---|---|
| 10 | B.2 | —N=CH—CH=CH— | —CH$_2$—C(CH$_3$)$_2$—CH$_2$— | — |
| 11 | B.2 | —N=CH—CH=CH— | —(CH$_2$)$_3$— | .C$_2$H$_2$O$_4$ (1:1) |

TABLE F-4

| Co No. | Ex. No. | —a¹=a²—a³=a⁴— | R⁶ | —Q— | Physical data (mp. in °C.) |
|---|---|---|---|---|---|
| 12 | B.4 | —N=CH—CH=CH— | benzyl | —CH$_2$—CO— | — |
| 13 | B.5 | —N=CH—CH=CH— | H | —CH$_2$—CO— | — |

TABLE F-5

| Co No. | Ex. No. | —a¹=a²—a³=a⁴— | —Alk¹—A— | —Q— | Physical data (mp. in °C.) |
|---|---|---|---|---|---|
| 14 | B.2 | —N=CH—CH=CH— | —CH$_2$—N(4-methylpiperidine)— | —(CH$_2$)$_2$— | — |
| 15 | B.1 | —N=CH—CH=CH— | —CH$_2$—N(4-methyl-4-hydroxymethylpiperidine)— | —(CH$_2$)$_3$— | mp. 160° C. |
| 16 | B.1 | —N=CH—CH=CH— | —CH$_2$—N(4-methyl-4-hydroxymethylpiperidine)— | —(CH$_2$)$_3$— | (A); mp. 160° C.; $[\alpha]_D^{20}$ = +30.11° (c = 23.75 mg/5 ml in methanol) |

TABLE F-5-continued

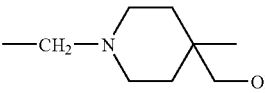

| Co No. | Ex. No. | —a¹=a²—a³=a⁴— | —Alk¹—A— | —Q— | Physical data (mp. in ° C.) |
|---|---|---|---|---|---|
| 17 | B.1 | —N=CH—CH=CH— | 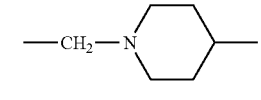 | —(CH$_2$)$_3$— | (B); mp. 165° C.; $[\alpha]_D^{20} = -30.11°$ (c = 9.30 mg/5 ml in methanol) |
| 18 | B.1 | —N=CH—CH=CH— | 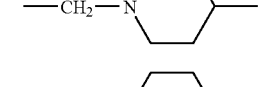 | —(CH$_2$)$_2$— | (A); mp. 132° C.; $[\alpha]_D^{20} = +38.88°$ (c = 24.95 mg/5 ml in methanol) |
| 19 | B.10 | —N=CH—CH=CH— | 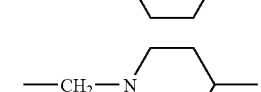 | —(CH$_2$)$_2$— | (S); mp. 132; $[\alpha]_D^{20} = -41.70°$ (c = 24.34 mg/5 ml in methanol |
| 20 | B.1 | —N=CH—CH=CH— | 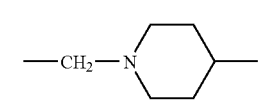 | —(CH$_2$)$_3$— | mp. 200° C. |
| 21 | B.1 | —N=CH—CH=CH— | 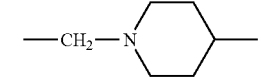 | —(CH$_2$)$_3$— | (A); mp. 195° C.; $[\alpha]_D^{20} = +38.51°$ (c = 25.97 mg/5 ml in methanol |
| 22 | B.10 | —N=CH—CH=CH— | 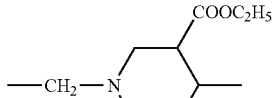 | —(CH$_2$)$_3$— | (S); mp. 195° C.; $[\alpha]_D^{20} = -41.90°$ (c = 24.82 mg/5 ml in methanol |
| 23 | B.2 | —N=CH—CH=CH— |  | —CH$_2$—CO— | .C$_2$H$_2$O$_4$ (1:1) |
| 31 | B.9 | —N=CH—CH=CH— | 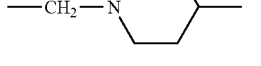 | —(CH$_2$)$_3$— | (A-trans), |
| 32 | B.9 | —N=CH—CH=CH— | 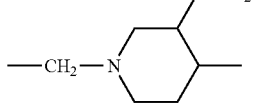 | —(CH$_2$)$_3$— | (B-trans); mp. 180° C. |
| 33 | B.9 | —N=CH—CH=CH— | 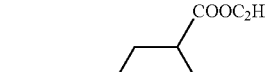 | —(CH$_2$)$_3$— | (A-cis); mp. 150° C. |
| 34 | B.9 | —N=CH—CH=CH— | 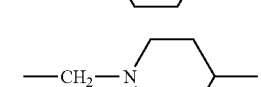 | —(CH$_2$)$_3$— | (B-cis) |
| 35 | B.3 | —CH=N—CH=CH— | 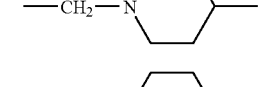 | —(CH$_2$)$_2$— | — |

TABLE F-5-continued

| Co No. | Ex. No. | —a$^1$=a$^2$—a$^3$=a$^4$— | —Alk$^1$—A— | —Q— | Physical data (mp. in ° C.) |
|---|---|---|---|---|---|
| 36 | B.3 | —CH=CH—N=CH— | —CH$_2$—N(piperidin-4-yl)— | —(CH$_2$)$_2$— | — |
| 37 | B.2 | —N=CH—CH=CH— | —CH$_2$—N(piperidin-4-yl)—CH$_2$— | —(CH$_2$)$_2$— | — |
| 38 | B.2 | —N=CH—C(CH$_3$)=CH— | —CH$_2$—N(piperidin-4-yl)— | —(CH$_2$)$_2$— | — |
| 39 | B.2 | —N=CCl—CH=CH— | —CH$_2$—N(piperidin-4-yl)— | —(CH$_2$)$_2$— | — |
| 40 | B.8 | —N(O)=CH—CH=CH— | —CH$_2$—N(piperidin-4-yl)— | —(CH$_2$)$_2$— | .H$_2$O (1:2) |
| 41 | B.3 | —N=CH—N=CH— | —CH$_2$—N(piperidin-4-yl)— | —(CH$_2$)$_2$— | — |
| 42 | B.2 | —N=CH—CH=CBr— | —CH$_2$—N(piperidin-4-yl)— | —(CH$_2$)$_2$— | (A) |
| 43 | B.9 | —N=CH—CH=CH— | —CH$_2$—N(3-OH-piperidin-4-yl)—CH$_2$— | —(CH$_2$)$_3$— | [B-[1(B),3ALPHA,4BETA]] |
| 44 | B.9 | —N=CH—CH=CH— | —CH$_2$—N(3-COOC$_2$H$_5$-piperidin-4-yl)— | —(CH$_2$)$_3$— | [B-[1(B),3ALPHA,4ALPHA]] |
| 45 | B.9 | —CH=N—CH=CH— | —CH$_2$—N(piperidin-4-yl)— | —(CH$_2$)$_2$— | (A); mp. 206° C. |
| 46 | B.9 | —CH=N—CH=CH— | —CH$_2$—N(piperidin-4-yl)— | —(CH$_2$)$_2$— | (B); mp. 206° C. |
| 47 | B.9 | —N=CH—CH=CH— | —CH$_2$—N(3-OH-piperidin-4-yl)—CH$_2$— | —(CH$_2$)$_3$— | [A-[1(B),3ALPHA,4BETA]] mp. 194 |

TABLE F-5-continued

| Co No. | Ex. No. | —a¹=a²—a³=a⁴— | —Alk¹—A— | —Q— | Physical data (mp. in ° C.) |
|---|---|---|---|---|---|
| 48 | B.9 | —N=CH—CH=CH— | —CH₂—N(piperidine, 4-methyl, 3-COOC₂H₅) | —(CH₂)₃— | [A-[1(B),3ALPHA,4ALPHA]] |
| 49 | B.6 | —N=CH—CH=CH— | —CH₂—N(piperidine, 4-methyl, 3-COOH) | —(CH₂)₃— | [A-[1(B),3ALPHA,4BETA]] |
| 50 | B.6 | —N=CH—CH=CH— | —CH₂—N(piperidine, 4-methyl, 3-COOH) | —(CH₂)₃— | [B-[1(B),3ALPHA,4BETA]] |
| 51 | B.7 | —N=CH—CH=CH— | —CH₂—N(piperidine, 4-methyl, 3-CH₂OH) | —(CH₂)₃— | [A-[1(B),3ALPHA,4ALPHA]] |

TABLE F-6

| Co No. | Ex. No. | —a¹=a²—a³=a⁴— | —Alk¹—A— | —Q— | Physical data (mp. in ° C.) |
|---|---|---|---|---|---|
| 24 | B.2 | —N=CH—CH=CH— | —CH₂—N(piperidine, 4-methyl) | —(CH₂)₂— | — |

TABLE F-7
| Co No. | Ex. No. | | —Q— | Physical data (mp. in ° C.) |
|---|---|---|---|---|
| 52 | B.2 | 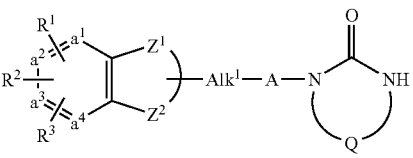 | —(CH$_2$)$_3$— | (A); .C$_2$H$_2$O$_4$ |
| 53 | B.2 | 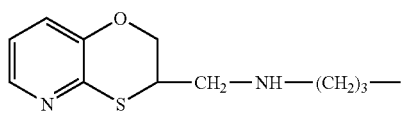 | —(CH$_2$)$_3$— | (B); .C$_2$H$_2$O$_4$ |
| 54 | B.2 | 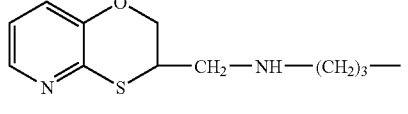 | —(CH$_2$)$_2$— | — |
| 55 | B.2 | 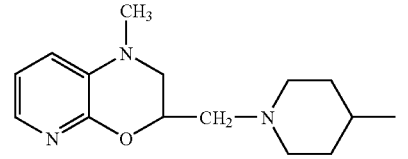 | —(CH$_2$)$_3$— | — |
| 56 | B.2 | 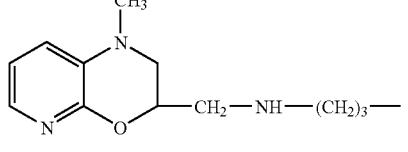 | —(CH$_2$)$_2$— | — |
| 57 | B.9 | 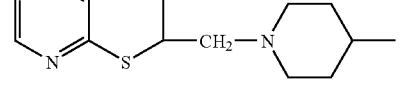 | —(CH$_2$)$_2$— | (A) |
| 58 | B.9 | 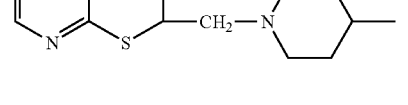 | —(CH$_2$)$_2$— | (B) |
| 59 | B.2 | 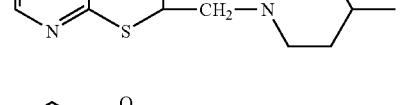 | —(CH$_2$)$_2$— | — |

C. Pharmacological Examples

C.1 Gastric Tone Measured by an Electronic Barostat in Conscious Dogs

Gastric tone cannot be measured by manometric methods. Therefore an electronic barostat was used. This allows the study of the physiological pattern and regulation of gastric tone in conscious dogs and the influence of test-compounds on this tone.

The barostat consists of an air injection system which is connected by a double-lumen 14-French polyvinyl tube to an ultrathin flaccid polyethylene bag (maximal volume: ±700 ml). Variations in gastric tone were measured by recording changes in the volume of air within an intragastric bag, maintained at a constant pressure. The barostat maintains a constant pressure (preselected) within a flaccid air-filled bag introduced into the stomach, changing the volume of air within the bag by an electronic feedback system.

Thus the barostat measures gastric motor activity (contraction or relaxation) as changes in intragastric volume (decrease or increase resp.) at a constant intragastric pressure. The barostat consists of a strain gauge linked by an electronic relay to an air injection-aspiration system. Both the strain gauge and the injection system are connected by means of double-lumen polyvinyl tube to an ultrathin polyethylene bag. A dial in the barostat allows selection of the pressure level to be maintained within the intragastric bag.

Female beagle dogs, weighing 7-17 kg, were trained to stand quietly in Pavlov frames. They were implanted with a gastric cannula under general anaesthesia and aseptic precautions. After a median laparotomy, an incision was made through the gastric wall in longitudinal direction between the greater and the lesser curve, 2 cm above the nerves of Latarjet. The cannula was secured to the gastric wall by means of a double purse string suture and brought out via a stub wound at the left quadrant of the hypochondrium. Dogs were allowed a recovery period of two weeks.

At the beginning of the experiment, the cannula was opened in order to remove any gastric juice or food remnants. If necessary, the stomach was cleansed with 40 to 50 ml lukewarm water. The ultrathin bag of the barostat was positioned into the fundus of the stomach through the gastric cannula. In order to ensure easy unfolding of the intragastric bag during the experiment, a volume of 300-400 ml was injected twice into the bag.

When during a stabilisation period of maximum 90 minutes, the gastric volume is stable during 15 minutes at a constant pressure of 6 mmHg (about 0.81 kPa), the test compound was administered subcutaneously (S.C.), or intraduodenally (I.D.). Test compounds were screened, i.e. changes in gastric volume were measured, usually at 0.63 mg/kg. Other doses and routes were tested if a test compound was shown to be active during the screening procedure. Table C-1 summarizes the mean maximal change in volume on relaxation of the fundus, during the 1 hour observation period after S.C. or I.D. administration of the test compound (0.63 mg/kg).

TABLE C-1

| Co. No. | Route | Maximum change in volume (ml) | Co. No. | Route | Maximum change in volume (ml) |
|---|---|---|---|---|---|
| 1 | S.C. | 156 | 16 | I.D. | 156 |
| 3 | I.D. | 245 | 18 | I.D. | 21 |
| 4 | S.C. | 327 | 22 | I.D. | 81* |
| 6 | I.D. | 301 | 24 | I.D. | 35 |
| 9 | S.C. | 78 | 25 | I.D. | 226* |
| 10 | S.C. | 31 | 30 | I.D. | 163* |
| 13 | I.D. | 118 | | | |

*maximum change in volume determined with a concentration of 0.04 mg/kg of test compound

C.2 Vasoconstrictive Activity on Basilar Artery

Segments of basilar arteries taken from pigs (anaesthetised with sodium pentobarbital) were mounted for recording of isometric tension in organ baths. The preparations were bathed in Krebs-Henseleit solution. The solution was kept at 37° C. and gassed with a mixture of 95% $O_2$-5% $CO_2$. The preparations were stretched until a stable basal tension of 2 grams was obtained.

The preparations were made to constrict with serotonin ($3 \times 10^{-7}$ M). The response to the addition of serotonin was measured and subsequently the serotonin was washed away. This procedure was repeated until stable responses were obtained. Subsequently the test compound was administered to the organ bath and the constriction of the preparation was measured. This constrictive response was expressed as a percentage of the response to serotonin as measured previously.

The $ED_{50}$-value (molar concentration) is defined as the concentration at which a test compound causes 50% of the constrictive response obtained with serotonin. Said $ED_{50}$-values are estimated from experiments on three different preparations.

The invention claimed is:

1. A compound of formula (I)

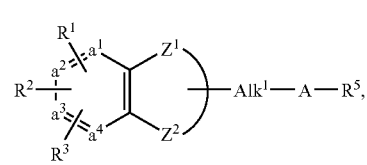

a stereochemically isomeric form thereof, an N-oxide form thereof, a pharmaceutically acceptable acid addition salt thereof, or a quaternary ammonium salt thereof, wherein -$a^1$=$a^2$-$a^3$=$a^4$- is a bivalent radical of formula

| —N=CH—CH=CH— | (a-1), |
|---|---|
| —CH=N—CH=CH— | (a-2), |
| —CH=CH—N=CH— | (a-3), |
| —CH=CH—CH=N— | (a-4); |

-$Z^1$-$Z^2$- is a bivalent radical of formula

—$Y^1$—CH($R^4$)—$CH_2$—O—     (b-3);

wherein, where possible, optionally one or two hydrogen atoms on the same or a different carbon or nitrogen atom may be replaced by hydroxy, $C_{1-4}$alkyloxy$C_{1-4}$alkyl, $C_{1-4}$alkylcarbonyl, or $C_{1-6}$alkyl optionally substituted with halo, hydroxy, $C_{3-6}$cycloalkyl or phenyl;

$Y^1$ is oxygen;

$Alk^1$ is $C_{1-4}$alkylcarbonyl, carbonyl$C_{1-4}$alkyl, $C_{1-4}$alkylcarbonyl$C_{1-4}$alkyl, carbonyl, or $C_{1-6}$alkanediyl optionally substituted with hydroxy, halo, amino, hydroxyC$_{1-4}$alkyl, C$_{1-4}$alkyloxy, hydroxycarbonyl, C$_{1-4}$alkyloxycarbonyl, aminocarbonyl, mono- or di(C$_{1-4}$ alkyl)aminocarbonyl, C$_{1-4}$alkyloxyC$_{1-4}$alkyl, C$_{1-4}$alkylcarbonyloxy, C$_{1-4}$alkylcarbonyloxyC$_{1-4}$alkyloxycarbonyloxy, C$_{1-4}$alkyloxyimino, phenylC$_{1-4}$alkylamino, C$_{1-4}$alkyloxycarbonylC$_{3-6}$alkenyl, cyanoC$_{3-6}$ alkenyl, or C$_{3-6}$cycloalkylcarbonyloxyC$_{1-4}$ alkyloxycarbonyloxy;

R$^1$, R$^2$ and R$^3$ are each independently selected from hydrogen, C$_{1-6}$alkyl, C$_{3-6}$alkenyl, C$_{1-6}$alkyloxy, hydroxycarbonyl, trihalomethyl, trihalomethoxy, halo, hydroxy, cyano, nitro, amino, C$_{1-6}$alkylcarbonylamino, C$_{1-6}$alkyloxycarbonyl, C$_{1-4}$alkylcarbonyloxy, aminocarbonyl, mono- or di(C$_{1-6}$alkyl)aminocarbonyl, aminoC$_{1-6}$alkyl, mono- or di(C$_{1-6}$alkyl)aminoC$_{1-6}$alkyl, C$_{1-4}$alkylcarbonyloxyC$_{1-4}$alkyloxy-carbonyloxy, or C$_{3-6}$cycloalkylcarbonyloxyC$_{1-4}$alkyloxycarbonyloxy;

R$^4$ is hydrogen, hydroxycarbonyl, phenyl, aminocarbonyl, mono- or di(C$_{1-4}$alkyl)aminocarbonyl, C$_{1-4}$alkyloxyC$_{1-4}$ alkyl, C$_{1-4}$alkyloxycarbonyl, N-pyrolidinylcarbonyl, N-piperidinylcarbonyl, N-homopiperidinylcarbonyl, C$_{1-4}$alkylcarbonyloxyC$_{1-4}$alkyloxycarbonyl, C$_{1-4}$alkyloxycarbonylC$_{1-4}$alkyl, C$_{3-6}$cycloalkylcarbonyloxyC$_{1-4}$ alkyloxycarbonyloxy, or C$_{1-6}$alkyl optionally substituted with hydroxy, cyano, amino, phenyl, mono- or di(C$_{1-4}$alkyl)amino, or mono- or di(C$_{1-4}$alkyl)aminocarbonyl;

-A- is a bivalent radical of formula

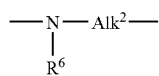
(c-1)

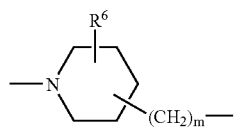
(c-2)

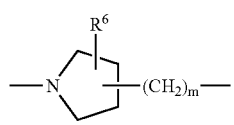
(c-3)

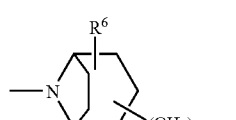
(c-4)

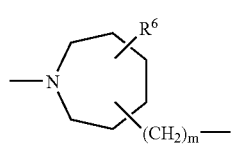
(c-5)

-continued

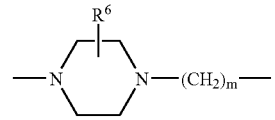
(c-6)

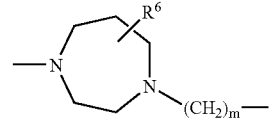
(c-7)

wherein m is 0 or 1;

Alk$^2$ is a bivalent radical independently selected from C$_{1-4}$alkylcarbonylC$_{1-4}$alkyl; phenyl; C$_{3-6}$cycloalkylcarbonyloxyC$_{1-4}$alkyloxycarbonyloxy; C$_{3-8}$cycloalkanediyl optionally substituted with one or more halo, hydroxy, hydroxycarbonyl, hydroxyC$_{1-4}$alkyl, C$_{1-4}$alkyloxy, C$_{1-4}$alkyloxyC$_{1-4}$alkyl, C$_{1-4}$alkyloxycarbonyl, C$_{1-4}$alkylcarbonyloxyC$_{1-4}$alkyloxycarbonyloxy, C$_{3-6}$cycloalkylcarbonyloxyC$_{1-4}$alkyloxycarbonyloxy, phenyl; or C$_{1-6}$alkyl optionally substituted with one or more hydroxy, halo, amino, hydroxycarbonyl, hydroxyC$_{1-4}$alkyl, C$_{1-4}$alkyloxy, C$_{1-4}$alkyloxyC$_{1-4}$alkyl, C$_{1-4}$alkyloxycarbonyl, C$_{1-4}$alkylcarbonyloxyC$_{1-4}$alkyloxycarbonyloxy, C$_{3-6}$cycloalkyl, aminocarbonyl, mono-or di(C$_{1-4}$alkyl)aminocarbonyl, or C$_{1-6}$alkyl wherein the C$_{1-6}$alkyl together with the carbon atom to which it is attached may form a C$_{3-6}$cycloalkyl;

R$^6$ is hydrogen, C$_{1-4}$alkyl, halo, hydroxy, hydroxyC$_{1-4}$alkyl, C$_{1-4}$alkyloxy, aminoC$_{1-4}$alkyl, C$_{1-4}$alkyloxycarbonyl, C$_{1-4}$alkylcarbonyloxyC$_{1-4}$alkyloxycarbonyl, amino, hydroxycarbonyl, aminocarbonyl, mono- or di(C$_{1-4}$alkyl)aminocarbonyl, or C$_{3-6}$cycloalkylcarbonyloxyC$_{1-4}$alkyloxycarbonyloxy;

R$^5$ is a radical of formula

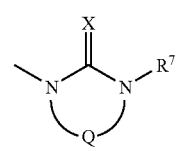
(d-1)

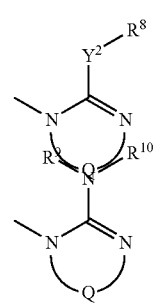
(d-2)

(d-3)

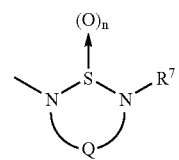
(d-4)

-continued

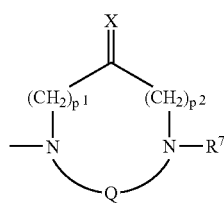
(d-5)

wherein n is 1 or 2;
p$^1$ is 0, and p$^2$ is 1 or 2; or p$^1$ is 1 or 2, and p$^2$ is 0;
X is oxygen, sulfur, NR$^9$ or CHNO$_2$;
Y$^2$ is oxygen or sulfur;
R$^7$ is hydrogen, C$_{1-6}$alkyl, C$_{3-6}$cycloalkyl, phenyl or phenylmethyl;
R$^8$ is C$_{1-6}$alkyl, C$_{3-6}$cycloalkyl, phenyl or phenylmethyl;
R$^9$ is cyano, C$_{1-6}$alkyl, C$_{3-6}$cycloalkyl, C$_{1-6}$alkyloxycarbonyl or aminocarbonyl;
R$^{10}$ is hydrogen or C$_{1-6}$alkyl;
or R$^9$ and R$^{10}$ taken together with the nitrogen atom to which they are attached may form a pyrrolidinyl, piperidinyl, homopiperidinyl, piperazinyl, or morpholinyl group, optionally substituted with C$_{1-4}$alkyl or C$_{1-4}$alkyloxy; and
Q is a bivalent radical of formula —CH$_2$—CH$_2$— (e-1), —CH$_2$—CH$_2$—CH$_2$— (e-2), —CH$_2$—CH$_2$—CH$_2$—CH$_2$— (e-3), —CH═CH— (e-4), —CH$_2$—CO— (e-5), —CO—CH$_2$ (e-6), —(CH$_2$)$_2$—CO— (e-7), —CO—(CH$_2$)$_2$— (e-8), —CO—CH$_2$—CO— (e-9), —CH$_2$—CO—CH$_2$— (e-10), wherein optionally one or two hydrogen atoms on the same or a different carbon atom may be replaced by C$_{1-4}$alkyl, hydroxyl or phenyl, or
Q is a bivalent radical of formula

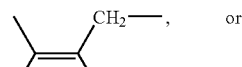
(e-11)

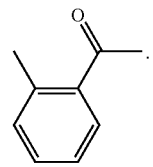
(e-12)

2. The compound as claimed in claim 1 wherein R$^5$ is a radical of formula (d-1) wherein X is oxygen, and Q is a radical of formula (e-2) or (e-5).

* * * * *

UNITED STATES PATENT AND TRADEMARK OFFICE
CERTIFICATE OF CORRECTION

PATENT NO.        : 7,423,048 B2                                      Page 1 of 1
APPLICATION NO.   : 11/355402
DATED             : September 9, 2008
INVENTOR(S)       : Kristof Van Emelen et al.

It is certified that error appears in the above-identified patent and that said Letters Patent is hereby corrected as shown below:

Title Page,
Item (75), Inventors:
Delete "Kristol Van Emelen," and insert -- Kristof Van Emelen, --.

Column 2,
Line 5, delete "–N=N–CH–H–    (a-5)," and insert -- –N=N–CH=CH–    (a-5), --.

Column 7,
Line 31, delete "(b-1)." and insert -- (b-11). --.

Column 19,
Line 35, delete "NHCl" and insert -- NH$_4$Cl --.

Column 44,
Lines 40-68, "(d-2) and (d-3)" have printed too close together. Leave space between each as follows:

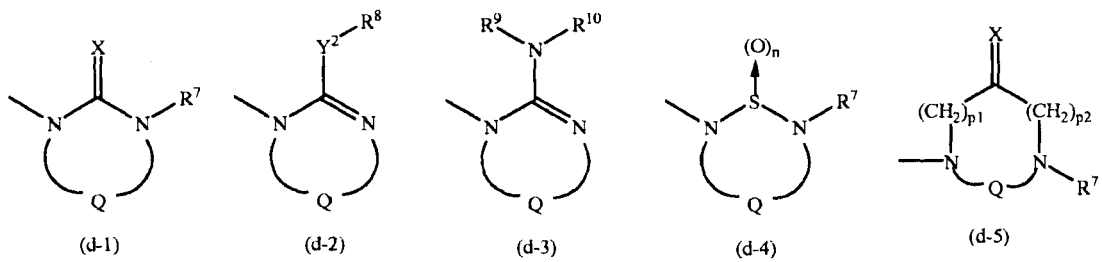

--                                                                    --.

Signed and Sealed this

Sixteenth Day of February, 2010

David J. Kappos
*Director of the United States Patent and Trademark Office*